United States Patent
Seitz et al.

(10) Patent No.: US 6,930,208 B2
(45) Date of Patent: Aug. 16, 2005

(54) 3-KETO- OR 3- OXIME-ETHER-SUBSTITUTED BENZOYLCYCLOHEXANEDIONES

(75) Inventors: Thomas Seitz, Viernheim (DE); Andreas van Almsick, Karben (DE); Lothar Willms, Hofheim (DE); Monika H. Schmitt, Frankfurt (DE); Thomas Auler, Bad Soden (DE); Hermann Bieringer, Eppstein (DE); Hubert Menne, Hofheim (DE)

(73) Assignee: Bayer CropScience GmbH, Frankfurt (DE)

( * ) Notice: Subject to any disclaimer, the term of this patent is extended or adjusted under 35 U.S.C. 154(b) by 31 days.

(21) Appl. No.: 10/409,340

(22) Filed: Apr. 8, 2003

(65) Prior Publication Data

US 2004/0204320 A1 Oct. 14, 2004

(30) Foreign Application Priority Data

Apr. 10, 2002 (DE) .......................... 102 15 723

(51) Int. Cl.$^7$ ..................... C07C 45/00; C07D 261/00; C07D 217/00; C07D 413/00; A01N 47/06
(52) U.S. Cl. ..................... 568/331; 568/337; 568/630; 568/63; 568/64; 548/240; 548/247; 548/494; 548/530; 546/146; 546/209; 546/272; 544/137; 544/298; 544/319; 504/306; 504/310
(58) Field of Search .................. 568/331, 337, 568/630, 63, 64; 548/240, 247, 494, 530; 546/146, 209, 272; 544/137, 298, 319; 504/306, 310

(56) References Cited

U.S. PATENT DOCUMENTS

| | | | | |
|---|---|---|---|---|
| 4,838,932 A | * | 6/1989 | Knudsen .......................... | 71/98 |
| 5,075,497 A | * | 12/1991 | Michaely et al. ............ | 562/429 |
| 6,054,414 A | | 4/2000 | Otten et al. | |
| 6,153,759 A | * | 11/2000 | von Deyn et al. .......... | 548/131 |
| 6,211,216 B1 | * | 4/2001 | Williams et al. ............ | 514/378 |
| 6,448,201 B1 | * | 9/2002 | Seitz et al. .................. | 504/130 |
| 6,703,348 B2 | * | 3/2004 | Almsick et al. ............ | 504/271 |
| 6,768,025 B2 | * | 7/2004 | Seitz et al. .................. | 568/331 |
| 6,774,086 B2 | * | 8/2004 | Seitz et al. .................. | 504/224 |

FOREIGN PATENT DOCUMENTS

| | | |
|---|---|---|
| DE | 42 23 015 A1 | 1/1994 |
| DE | 100 39 723 A1 | 7/2001 |
| EP | 0 319 075 A2 | 6/1989 |
| WO | WO 92/07837 | 5/1992 |
| WO | WO 96/22958 | 8/1996 |
| WO | WO 98/42648 | 10/1998 |
| WO | WO-01/53275 A2 | 7/2001 |

OTHER PUBLICATIONS

English language abstract of DE–42 23 015–A1 (2001).

* cited by examiner

*Primary Examiner*—Johann Richter
*Assistant Examiner*—Sikarl A. Witherspoon
(74) *Attorney, Agent, or Firm*—Connolly Bove Lodge & Hutz LLP

(57) ABSTRACT

What is described are derivatives of benzoylcyclohexanediones of the formula (I) and their use as herbicides.

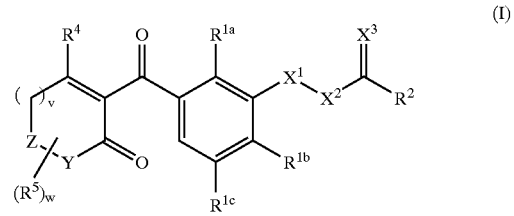

In this formula (I), $R^{1a}$, $R^{1b}$, $R^{1c}$, $R^2$, $R^3$, $R^4$ and $R^5$ denote various radicals, $X^1$ is a bridging atom, $X^2$ is a carbon chain and $X^3$ is a chalcogen atom or an oximino radical.

16 Claims, No Drawings

3-KETO- OR 3- OXIME-ETHER-SUBSTITUTED BENZOYLCYCLOHEXANEDIONES

DESCRIPTION

3-Keto- or 3-oxime-ether-substituted benzoylcyclohexanediones

The invention relates to the technical field of the herbicides, in particular that of the herbicides from the benzoylcyclohexanedione group, for the selective control of broad-leaved weeds and weed grasses in crops of useful plants, in particular in rice crops.

It has already been disclosed in a variety of publications that certain benzoylcyclohexanediones have herbicidal properties. Thus, EP-A 0 319 075, WO 92/07837 and WO 96/22958 disclose benzoylcyclohexanediones having a haloalkoxy radical in the 3-position of the phenyl ring. WO 98/42648 mentions benzoylcyclohexanediones which have a variety of amino radicals attached to them in the 3-position. The German patent application DE 10144529.6 which has priority but has not yet been published, describes benzoylcyclohexanediones having an aminocarbonyl group attached via a polyatomic unit in the 3-position of the phenyl ring.

However, the herbicidal activity of the compounds known from these publications is frequently insufficient. It is therefore an object of the present invention to provide herbicidally active compounds having herbicidal properties which are better than those of the compounds disclosed in the prior art.

It has now been found that derivatives of benzoylcyclohexanediones whose phenyl ring carries in the 3-position—attached to the phenyl ring via an atom selected from the group consisting of oxygen, sulfur and nitrogen—a keto or oxime ether radical, are particularly suitable for use as herbicides. Part of the subject-matter of the present invention are therefore compounds of the formula (I) and salts thereof

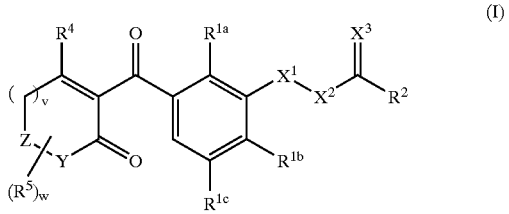

(I)

where the radicals and indices are as defined below:

$X^1$ is a divalent unit selected from the group consisting of O, $S(O)_n$, N—H, N—$R^2$;

$X^2$ is a straight-chain or branched $(C_1-C_6)$-alkylene, $(C_2-C_6)$-alkenylene or $(C_2-C_6)$-alkynylene chain which is substituted by w radicals selected from the group consisting of halogen, cyano and $NO_2$ and by v radicals $R^2$;

$X^3$ is oxygen, sulfur or $NOR^3$;

$R^{1a}$, $R^{1b}$ and $R^{1c}$ independently of one another are H, mercapto, $NO_2$, halogen, cyano, thiocyanato, $(C_1-C_6)$-alkyl-CO—O, $(C_1-C_6)$-alkyl-$S(O)_n$—O, $(C_1-C_6)$-alkyl-$S(O)_n$, $(C_1-C_6)$-haloalkyl-$S(O)_n$, $(C_3-C_7)$-cycloalkyl-$S(O)_n$, di-$(C_1-C_6)$-alkyl-N-$SO_2$, $(C_1-C_6)$-alkyl-$SO_2$—NH, $(C_1-C_6)$-alkyl-NH—CO, di-$(C_1-C_6)$-alkyl-N—CO, $(C_1-C_6)$-alkyl-$SO_2$-$(C_1-C_6)$-alkyl-NH, $(C_1-C_6)$-alkyl-CO-$(C_1-C_6)$-alkyl-NH, $(C_1-C_6)$-alkyl-O—$CH_2$, $(C_1-C_6)$-alkyl-$S(O)_n$—$CH_2$, $(C_1-C_6)$-alkyl-NH—$CH_2$, 1,2,4-triazol-1-yl, 1,2,4-triazol-1-yl-$CH_2$, are $(C_1-C_6)$-alkyl-$(D)_p$, $(C_2-C_6)$-alkenyl-$(D)_p$, $(C_2-C_6)$-alknyl-$(D)_p$, $(C_3-C_9)$-cycloalkyl-$(D)_p$, $(C_3-C_9)$-cycloalkenyl-$(D)_p$, $(C_1-C_6)$-alkyl-cycloalkyl-$(D)_p$, $(C_1-C_6)$-alkyl-cycloalkenyl-$(D)_p$, each of which is substituted by v radicals selected from the group consisting of CN, $NO_2$ and halogen;

D is oxygen or sulfur;

$R^2$, $R^3$ independently of one another are hydrogen, $(C_1-C_6)$-alkyl, $(C_2-C_6)$-alkenyl, $(C_2-C_6)$-alkynyl, $(C_3-C_9)$-cycloalkyl, $(C_3-C_9)$-cycloalkenyl, $(C_1-C_6)$-alkyl-$(C_3-C_9)$-cycloalkyl, $(C_1-C_6)$-alkyl-$(C_3-C_9)$-cycloalkenyl, $(C_2-C_6)$-alkenyl-$(C_3-C_9)$-cycloalkyl, $(C_2-C_6)$-alkenyl-$(C_3-C_9)$-cycloalkenyl, $(C_2-C_6)$-alkynyl-$(C_3-C_9)$-cycloalkyl, $(C_2-C_6)$-alkynyl-$(C_3-C_9)$-cycloalkenyl or straight-chain or branched $[C(R^6)_2]_z$—$[OC(R^6)_2]_w$—$[O$—$C(R^6)_2]_x$—$R^6$, each of which is substituted by v radicals selected from the group consisting of CN, $NO_2$ and halogen, aryl, $(C_1-C_6)$-alkyl-aryl, $(C_2-C_6)$-alkenyl-aryl, $(C_2-C_6)$-alkynyl-aryl, heterocyclyl or heteroaryl, each of which is substituted by v radicals selected from the group consisting of CN, $NO_2$, halogen, $(C_1-C_6)$-alkyl-$(D)_p$ and halo-$(C_1-C_6)$-alkyl-$(D)_p$;

$R^4$ is $OR^7$, $(C_1-C_4)$-alkylthio, halo-$(C_1-C_4)$-alkylthio, $(C_2-C_4)$-alkenylthio, halo-$(C_2-C_4)$-alkenylthio, $(C_2-C_4)$-alkynylthio, halo-$(C_2-C_4)$-alkynylthio, $(C_1-C_4)$-alkyl-SO, halo-$(C_1-C_4)$-alkyl-SO, $(C_2-C_4)$-alkenyl-SO, halo-$(C_2-C_4)$-alkenyl-SO, $(C_2-C_4)$-alkynyl-SO, halo-$(C_2-C_4)$-alkynyl-SO, $(C_1-C_4)$-alkyl-$SO_2$, halo-$(C_1-C_4)$-alkyl-$SO_2$, $(C_2-C_4)$-alkenyl-$SO_2$, halo-$(C_2-C_4)$-alkenyl-$SO_2$, $(C_2-C_4)$-alkynyl-$SO_2$, halo-$(C_2-C_4)$-alkynyl-$SO_2$, halogen, CN, cyanato, thiocyanato or phenylthio;

$R^5$ is hydrogen, tetrahydropyran-3-yl, tetrahydropyran-4-yl, tetrahydrothiopyran-3-yl, $(C_1-C_4)$-alkyl, $(C_1-C_8)$-cycloalkyl, $(C_1-C_4)$-alkoxy, $(C_1-C_4)$-alkoxy-$(C_1-C_4)$-alkyl, $(C_1-C_4)$-alkoxy-CO, $(C_1-C_4)$-alkylthio or phenyl, each of which is substituted by v radicals selected from the group consisting of halogen, $(C_1-C_4)$-alkylthio and $(C_1-C_4)$-alkoxy, or two radicals $R^5$ attached to a common carbon atom form a chain selected from the group consisting of $OCH_2CH_2O$, $OCH_2CH_2CH_2O$, $SCH_2CH_2S$ and $SCH_2CH_2CH_2S$, which is substituted by w methylene groups, or two radicals $R^5$ attached to directly adjacent carbon atoms form, together with the carbon atoms carrying them, a 3- to 6-membered ring substituted by w radicals selected from the group consisting of halogen, $(C_1-C_4)$-alkyl, $(C_1-C_4)$-alkylthio and $(C_1-C_4)$-alkoxy;

$R^6$ is H, halogen, CN, $NO_2$, $(C_1-C_4)$-alkyl or halo-$(C_1-C_4)$-alkyl;

$R^7$ is H, $(C_1-C_4)$-alkyl, halo-$(C_1-C_4)$-alkyl, $(C_1-C_4)$-alkoxy-$(C_1-C_4)$-alkyl, CHO, $(C_1-C_4)$-alkyl-CO, $(C_1-C_4)$-alkoxy-CO, $(C_1-C_4)$-alkyl-NH—CO, di-$(C_1-C_4)$-alkyl-N—CO, $(C_1-C_4)$-alkyl-$SO_2$, halo-$(C_1-C_4)$-alkyl-$SO_2$, is benzoyl or phenyl-$SO_2$, each of which is substituted by v radicals selected from the group consisting of $(C_1-C_4)$-alkyl, halo-$(C_1-C_4)$-alkyl, $(C_1-C_4)$-alkoxy, halo-$(C_1-C_4)$-alkoxy, halogen, CN and $NO_2$;

Y is a divalent unit selected from the group consisting of O, S, N—H, $(C_1-C_6)$-alkyl-N, $CHR^5$ and $C(R^5)_2$;

Z is a direct bond or a divalent unit selected from the group consisting of O, S, SO, $SO_2$, N—H, $(C_1-C_6)$-alkyl-N, $CHR^6$ and $C(R^6)_2$;

m and n are each independently of one another 0, 1 or 2;

p is independently of the other p 0 or 1;

v is 0, 1, 2 or 3;

w and x are each independently of one another 0, 1, 2, 3 or 4;

z is 1, 2, 3 or 4, where w and x are not simultaneously zero.

In the event that $R^4$ is OH, the compounds of the formula (I) according to the invention can exist in different tautomeric structures, depending on the external conditions such as solvent and pH. Depending on the nature of the substituents, the compounds of the formula (I) contain an acidic proton, which can be removed by reaction with a base. Examples of suitable bases are hydrides, hydroxides and carbonates of alkali and alkaline earth metals, such as lithium, sodium, potassium, magnesium and calcium, and also ammonia and organic amines such as triethylamine and pyridine. The invention likewise relates to such salts.

In formula (I) and all subsequent formulae, alkyl radicals with more than two carbon atoms can be straight-chain or branched. Alkyl radicals are, for example, methyl, ethyl, n- or i-propyl, n-, i-, t- or 2-butyl, pentyls, hexyls such as n-hexyl, i-hexyl and 1,3-dimethylbutyl. Likewise, the carbon chain $X^2$ can be straight-chain or branched, depending on the number of carbon atoms which it contains. It is, for example, —CH$_2$—, —CH$_2$CH$_2$—, —CH$_2$CH$_2$CH$_2$—, —CH$_2$CH(CH$_3$)—, —CH(CH$_3$)CH$_2$—, —CH=CH$_2$—, —CH$_2$CH=CH$_2$—, —CH=CHCH$_2$—, —CH≡CHCH$_2$—, CH≡CHCH$_2$—. The radicals bonded thereto can in principle be in any desired position of this chain.

If a group is polysubstituted by radicals, this is understood as meaning that this group is substituted by one or more of the abovementioned radicals, which may be identical or different.

Cycloalkyl is a carbocyclic saturated ring system with three to nine carbon atoms, for example cyclopropyl, cyclopentyl or cyclohexyl. Analogously, cycloalkenyl is a monocyclic alkenyl group having three to eight carbon ring members, for example cyclopropenyl, cyclobutenyl, cyclopentyl and cyclohexenyl, it being possible for the double bond to be in any desired position. In the case of composite radicals, such as cycloalkylalkenyl, the first-mentioned radical may be in any desired position of the second-mentioned radical.

In the case of a disubstituted amino group, such as dialkylamino, these two substituents can be identical or different.

Halogen is fluorine, chlorine, bromine or iodine. Haloalkyl, -alkenyl and -alkynyl are alkyl, alkenyl or alkynyl, each of which is partially or fully substituted by halogen, preferably by fluorine, chlorine and/or bromine, in particular by fluorine or chlorine, for example CF$_3$, CHF$_2$, CH$_2$F, CF$_3$CF$_2$, CH$_2$FCHCl, CCl$_3$, CHCl$_2$, CH$_2$CH$_2$Cl; haloalkoxy is, for example, OCF$_3$, OCHF$_2$, OCH$_2$F, CF$_3$CF$_2$O, OCH$_2$CF$_3$ and OCH$_2$CH$_2$Cl; this also applies analogously to haloalkenyl and other halogen-substituted radicals.

The term heterocyclyl is understood as meaning three- to six-membered, saturated or partially unsaturated mono- or polycyclic heterocycles containing one to three hetero atoms selected from a group consisting of oxygen, nitrogen and sulfur. If chemically possible, the linkage can be effected at any desired position of the heterocycle. Examples are oxiranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothioazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 1-morpholinyl, 2-morpholinyl, 3-morpholinyl, 1-piperidinyl, 2-piperidinyl, 3-piperidinyl, 4-piperidinyl, 3-tetrahydropyridazinyl, 4-tetrahydropyridazinyl, 2-tetrahydro-pyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,3-dithian-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl.

Aryl is an aromatic mono- or polycyclic hydrocarbon radical, for example phenyl, naphthyl, biphenyl and phenanthryl, preferably phenyl. In principle, the linkage may be effected at any desired position of the aryl.

Heteroaryl is an aromatic mono-, bi- or tricyclic radical which, in addition to carbon ring members, contains one to four nitrogen atoms or one to three nitrogen atoms and one oxygen or one sulfur atom or an oxygen or a sulfur atom. If chemically possible, the linkage can be effected at any desired position of the aryl. Examples of 5-membered heteroaryl are 2-pyrrolyl, 3-pyrrolyl, 1-pyrazolyl, 3-pyrazolyl, 4-pyrazolyl, 5-pyrazolyl, 2-imidazolyl, 4-imidazolyl, 1,2,4-triazol-3-yl, 1,3,4-triazol-2-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl. Examples of 6-membered heteroaryl are 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl. Examples of fused 5-membered heteroaryl are benzothiazol-2-yl and benzoxazol-2-yl. Examples of benzofused 6-membered heteroaryl are quinoline, isoquinoline, quinazoline and quinoxaline.

If a group is polysubstituted, this is understood as meaning that, when the different substituents are combined, the general principles of the structure of chemical compounds must be observed, that is to say no compounds must be formed which are known to the skilled worker as being chemically unstable or impossible.

Depending on the type and linkage of the substituents, the compounds of the formula (I) can exist as stereoisomers. If, for example, one or more asymmetric carbon atoms are present, enantiomers and diastereomers may occur. Stereoisomers can be obtained from the mixtures resulting from the preparation by means of customary separation methods, for example by chromatographic separation methods. Likewise, stereoisomers may be prepared selectively by using stereoselective reactions and optically active starting materials and/or adjuvants. The invention also relates to all of the stereoisomers and their mixtures which are encompassed by the formula (I), but not defined specifically.

Compounds of the formula (I) which have proved advantageous are those in which $R^2$, $R^3$ independently of one another are hydrogen, $(C_1-C_6)$-alkyl, $(C_2-C_6)$-alkenyl, $(C_2-C_6)$-alkynyl, $(C_3-C_9)$-cycloalkyl, $(C_3-C_9)$-cycloalkenyl, $(C_1-C_6)$-alkyl-$(C_3-C_9)$-cycloalkyl, $(C_1-C_6)$-alkyl-$(C_3-C_9)$-cycloalkenyl, $(C_2-C_6)$-alkenyl-$(C_3-C_9)$-cycloalkyl, $(C_2-C_6)$-alkenyl-$(C_3-C_9)$-cycloalkenyl, $(C_2-C_6)$-alkynyl-$(C_3-C_9)$-cycloalkyl, $(C_2-C_6)$-alkynyl-$(C_3-C_9)$-cycloalkenyl or straight-chain or branched $[C(R^6)_2]_z$—$[OC(R^6)_2]_w$—$[O—C(R^6)_2]_x$—$R^6$, each of which is substituted by v radicals selected from the group consisting of CN, $NO_2$ and halogen, aryl, $(C_1-C_6)$-alkyl-aryl, $(C_2-C_6)$-alkenyl-aryl or $(C_2-C_6)$-alkynyl-aryl, each of which is substituted by v radicals selected from the group consisting of CN, $NO_2$, halogen, $(C_1-C_6)$-alkyl-$(D)_p$ and halo-$(C_1-C_6)$-alkyl-$(D)_p$.

Also advantageous are compounds of the formula (I) in which
$X^3$ is nitrogen or $NOR^3$, and
$R^{1c}$ is hydrogen.

Preference is given to compounds of the formula (I) in which
$X^1$ is oxygen or $S(O)_n$;
$R^{1a}$, $R^{1b}$ are independently of one another F, Cl, Br, $NO_2$, $CF_3$, $CH_3$, $CH_3S$, $CH_3O$, $CH_3SO_2$, $EtSO_2$, $CF_3CH_2SO_2$ or cyclopropyl-$SO_2$, and
$R^2$, $R^3$ are independently of one another hydrogen, $(C_1-C_6)$-alkyl, $(C_2-C_6)$-alkenyl, $(C_2-C_6)$-alkynyl, $(C_3-C_9)$-cycloalkyl, $C_1-C_6$-alkyl-$(C_3-C_9)$-cycloalkyl, straight-chain or branched $[C(R^6)_2]_z$—$[OC(R^6)_2]_w$—$[O—C(R^6)_2]_x$—$R^6$, each of which is substituted by v radicals selected from the group consisting of CN, $NO_2$ and halogen,
aryl or $(C_1-C_6)$-alkyl-aryl, each of which is substituted by v radicals selected from the group consisting of CN, $NO_2$, halogen, $(C_1-C_6)$-alkyl-$(D)_p$ and halo-$(C_1-C_6)$-alkyl-$(D)_p$.

Preference is also given to compounds of the formula (I) in which
$X^1$ is oxygen and
$R^4$ is $OR^7$, $(C_1-C_4)$-alkylthio, $(C_2-C_4)$-alkenylthio, $(C_1-C_4)$-alkyl-$SO_2$, halogen, CN, cyanato, thiocyanato or phenylthio.

Particular preference is given to compounds of the formula (I) in which
$R^5$ is hydrogen or $(C_1-C_4)$-alkylthio.

Particular preference is also given to compounds of the formula (I) in which
$R^4$ is $OR^7$;
D is oxygen;
Y, Z are each $CH_2$;
v, w and x are each independently of one another 0, 1 or 2;
z is 1 or 2.

In all of the formulae stated hereinbelow, the substituents and symbols have the same meaning as defined under formula (I), unless otherwise defined.

Compounds according to the invention in which $R^4$ is OH can be prepared for example in accordance with the method shown in scheme 1 by reacting, with base catalysis, a compound of the formula (IIIa) in which T is halogen, hydroxyl or alkoxy with a cyclohexanedione (II) in the presence of a cyanide source. Such methods are described, for example, in EP-A 0 186 117.

Scheme 1:

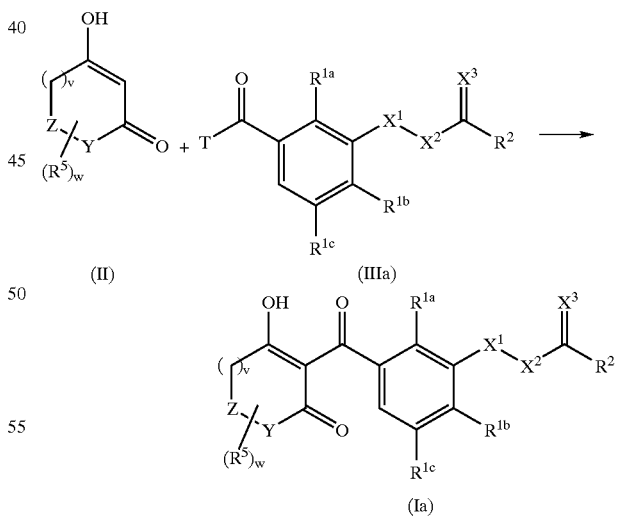

Compounds of the formula (IIIa) can be prepared for example in accordance with scheme 2 from compounds of the formula (IIIb) in which T is hydroxy or alkoxy and (IVa) in which $L^1$ is a leaving group such as halogen, mesyl, tosyl or triflate, by methods known per se. Such methods are known for example from Houben-Weyl Volume 6/3, pp. 54 to 69, Volume 9, pp. 103 to 115 and Volume 11, p. 97.

Scheme 2:

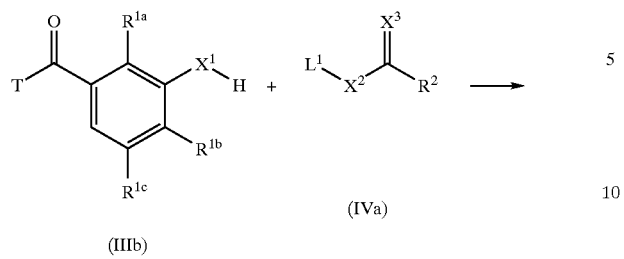 + 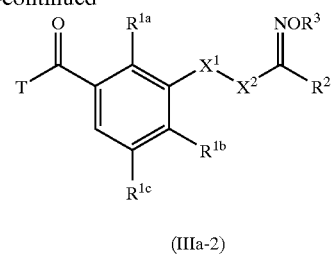 →

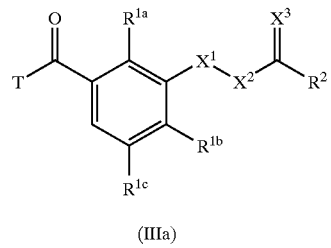

(IIIa)

Compounds of the formula (IIIa-2) in which $X^3$ is $NOR^3$ can also be prepared according to scheme 3 by reacting compounds of the formula (IIIa-1) with hydroxylamine derivatives of the formula (IVb). Such methods are known, for example, from Houben-Weyl Volume 10/4, pp. 55 to 76.

Scheme 3:

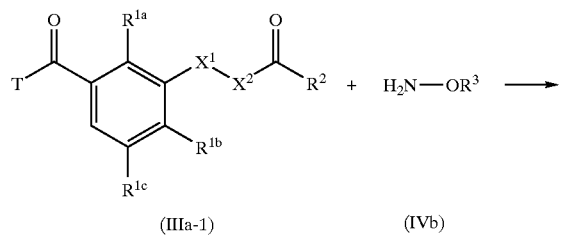

(IIIa-2)

Compounds of the formula (I) according to the invention in which $R^4$ represents radicals other than hydroxyl can be prepared for example in accordance with scheme 4. The reaction of a compound of the formula (Ia) with a halogenating reagent such as oxalyl chloride or oxalyl bromide, which is shown in this scheme, yields compounds of the formula (Ib), according to the invention, which can be converted into further compounds of the formula (Ic) according to the invention in which $R^4$ is alkylthio, haloalkylthio, alkenylthio, haloalkenylthio, alkynylthio, haloalkynylthio, optionally substituted phenylthio, cyano, cyanato, thiocyanato or $OR^7$ by reaction with nucleophiles, such as alkali metal cyanides, alkali metal cyanates, alkali metal thiocyanates, alkyl thioalcohols and thiophenols, if appropriate with base catalysis. Such reactions are described, for example, in *Synthesis* 12, 1287 (1992). The reaction with an oxidant, such as m-chloroperbenzoic acid, peroxyacetic acid, hydrogen peroxide and potassium peroxymonosulfate, gives compounds of the formula (Ic) according to the invention in which $R^4$ is alkylsulfinyl, haloalkylsulfinyl, alkenylsulfinyl, haloalkenylsulfinyl, alkynylsulfinyl, haloalkynylsulfinyl, alkylsulfonyl, haloalkylsulfonyl, alkenylsulfonyl, haloalkenylsulfonyl, alkynylsulfonyl, optionally substituted phenylthio or haloalkynylsulfonyl. Such reactions are described, for example, in *J. Org. Chem.* 53, 532 (1988), *Tetrahedron Lett.* 21, 1287 (1981).

Scheme 4:

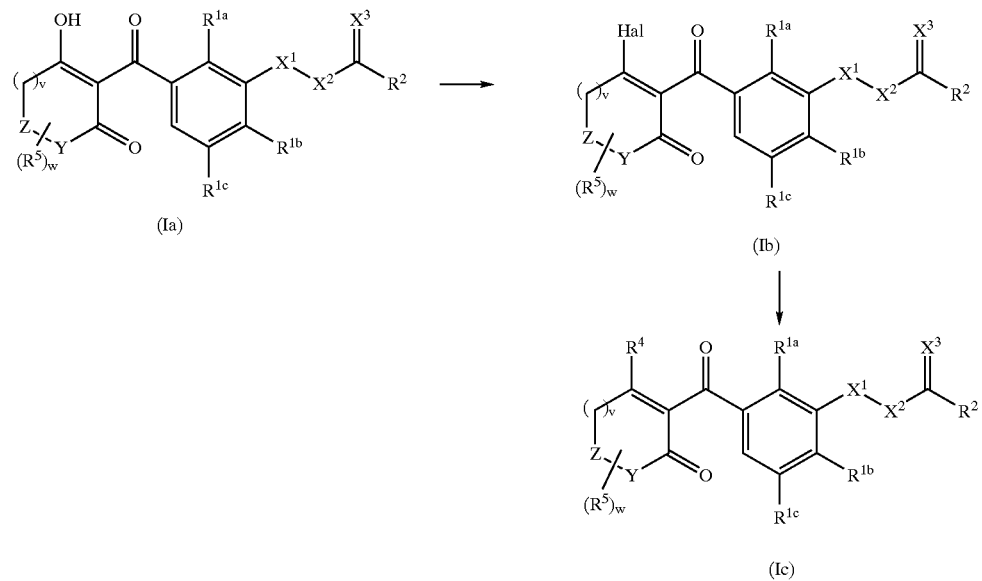

Compounds of the formula (IVa) can be prepared, for example, according to scheme 5 from compounds of the formula (VII) in which L² is a group such as chlorine and L¹ is a group such as chlorine, bromine, mesyl or tosyl with organometallic reagents of the formula (VIII) in which Met is a metal such as magnesium, cadmium or zinc, according to methods known per se. Such methods are known, for example, from Organic Reactions 8 (1954) 28; *J. Org. Chem.* 28 (1963) 630; Zh. Org. Khim. 27 (1991) 7, 1431.

Scheme 5:

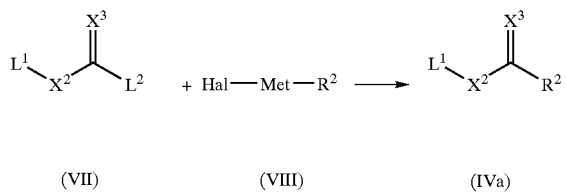

Compounds of the formula (IVa-1) in which $X^3$ represents $NOR^3$ can also be prepared, for example, according to scheme 6 from compounds of the formula (IX) by reaction with a hydroxylamine derivative of the formula (IVb) according to methods known to the person skilled in the art. Such methods are described, for example, in Houben-Weyl, Volume 10/4, pp. 55–76; J. Chem. Soc. Perkin Trans. 1, 7 (1991) 1721.

Scheme 6:

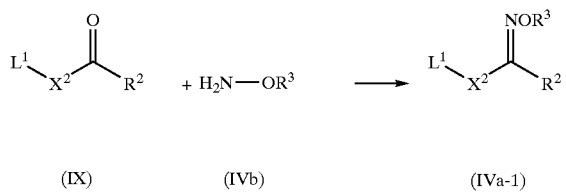

The compounds of the formula (I) according to the invention have an excellent herbicidal activity against a broad range of economically important monocotyledonous and dicotyledonous harmful plants. The active substances control perennial weeds equally well which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the perennial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennials. Harmful plants which are found under the specific culture conditions of rice, such as, for example, *Echinochloa, Sagittaria, Alisma, Eleocharis, Scirpus* and *Cyperus* are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that competition by the weeds, which is detrimental for the crop plants, is thus eliminated at a very early stage and in a sustained manner. In particular, the compounds according to the invention have an outstanding action against *Amaranthus retroflexus, Avena* sp., *Echinochloa* sp., *Cyperus serotinus, Lolium multiflorum, Setaria viridis, Sagittaria pygmaea, Scirpus juncoides, Sinapis* sp. and *Stellaria media*.

Although the compounds according to the invention have an outstanding herbicidal activity against monocotyledonous and dicotyledonous weeds, crop plants of economically important crops such as, for example, wheat, barley, rye, rice, maize, sugar beet, cotton and soya, only suffer negligible damage, if any. In particular, they are outstandingly well tolerated in wheat, maize and rice. This is why the present compounds are highly suitable for the selective control of undesired vegetation in stands of agricultural useful plants or of ornamentals.

Owing to their herbicidal properties, the active substances can also be employed for controlling harmful plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased starch content or whose starch quality has been modified, or those whose fatty acid spectrum in the harvested material is different.

The compounds of the formula (I) according to the invention or their salts are preferably employed in economically important transgenic crops of useful plants and ornamentals, for example cereals such as wheat, barley, rye, oats, sorghum and millet, rice, cassava and maize, or else crops of sugar beet, cotton, soya, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:
  recombinant modifications of crop plants for the purposes of modifying the starch synthesized in the plants (for example WO 92/11376, WO 92/14827, WO 91/19806),
  transgenic crop plants which exhibit resistances to certain herbicides of the glufosinate type (cf. eg. EP-A-

0242236, EP-A-242246), glyphosate type (WO 92/00377) or of the sulfonylurea type (EP-A-0257993, US-A-5013659)

transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid spectrum (WO 91/13972), A large number of techniques in molecular biology, with the aid of which novel transgenic plants with modified properties can be generated, are known in principle; see, for example, Sambrook et al., 1989, Molecular Cloning, A Laboratory Manual, $2_{nd}$ Ed., Cold Spring Harbor Laboratory Press, Cold Spring Harbor, N.Y.; or Winnacker "Gene und Klone" [Genes and Clones], VCH Weinheim $2_{nd}$ Edition 1996 or Christou, "Trends in Plant Science" 1 (1996) 423–431.

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give intact plants. In principle, the transgenic plants can be plants of any desired plant species, i.e. both monocotyledonous and dicotyledonous plants.

Thus, transgenic plants can be obtained which exhibit modified properties owing to the overexpression, suppression or inhibition of homologous (=natural) genes or gene sequences or expression of heterologous (=foreign) genes or gene sequences.

When using the active substances according to the invention in transgenic crops, effects are frequently observed in addition to the effects against harmful plants to be observed in other crops, which are specific for the application in the transgenic crop in question, for example a modified or specifically widened weed spectrum which can be controlled, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling harmful plants in transgenic crop plants.

The substances according to the invention additionally have outstanding growth-regulatory properties in crop plants. They engage in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since lodging can be reduced, or prevented completely, hereby.

The compounds according to the invention can be employed in the form of wettable powders, emulsifiable concentrates, sprayable solutions, dusts or granules in the customary preparations. The invention therefore furthermore relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Engineering], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, e.g. butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water based or oil based. They can be prepared for example by wet-grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, N.Y. 1973, pp. 8–57.

For further details on the formulation of crop protection products see, for example G.C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight.

Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the tackifiers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441–445 (1986) or "The Pesticide Manual", 11th edition, The British Crop Protection Council and the Royal Soc. of Chemistry, 1997 and literature cited therein. Known herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number): acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluorine-2-phenyl-4H-3,1-benzoxazin-4-one; benazolin; benfluralin; benfuresate; bensulfuronmethyl; bensulide; bentazone; benzofenap; benzofluor; benzoylpropethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICl-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICl-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthaldimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron;ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentylester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachior; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are present in commercially available form, are diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use. The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. Chemical Examples

The starting compound ethyl 2,4-dibromo-3-hydroxybenzoate was prepared as described in U.S. Pat. No. 5,026,896, and 2-chloro-3-hydroxy-4-ethylsulfonylbenzoic acid was prepared as described in EP-A 0 195 247.

The abbreviation RT stands for room temperature. $R_f$ is the retention value.

a) Preparation of (2-chloro-3-(methylcarbonyl methoxy)-4-ethylsulfonylbenzoyl)-cyclohexane-1,3-dione (tabulated example No. 3.3)

Step 1: Methyl 2-chloro-3-hydroxy-4-ethylsulfonylbenzoate 33.0 g (124.7 mmol) of 2-chloro-3-hydroxy-4-ethylsulfonylbenzoic acid were dissolved in 1 300 ml of methanol. 174 ml (3 263 mmol) of concentrated $H_2SO_4$ were added dropwise, and the mixture was refluxed for 5 hours. The reaction mixture was concentrated and the residue was taken up in $CH_2Cl_2$. The product was washed with water, dried over $Na_2SO_4$ and evaporated to dryness. This gave methyl 2-chloro-3-hydroxy-4-ethylsulfonylbenzoate as a yellow viscous oil.

Yield: 28.23 g (81% of theory) $R_f$: (ethyl acetate) 0.45
$^1$H-NMR: δ [$CDCl_3$] 1.32 (t, 3H), 3.24 (q, 2H), 3.96 (s, 3H), 7.38 (d, 1H), 7.65 (d, 1H)

Step 2: Methyl 2-chloro-3-(methylcarbonylmethoxy)-4-ethylsulfonylbenzoate 0.922 g (7.2 mmol) of $K_2CO_3$, 0.179 g (1.10 mmol) of KI and 0.454 g (4.7 mmol) of chloroacetone were introduced into 30 ml of DMF. 1.000 g (3.6 mmol) of methyl 2-chloro-3-hydroxy-4-ethylsulfonylbenzoate were added at RT and the mixture was then heated for 4 hours at 80° C. The mixture was then poured into water and extracted with diisopropyl ether. The combined organic phases were washed with water, dried over $Na_2SO_4$ and evaporated to dryness. The resulting crude methyl 2-chloro-3-(methylcarbonylmethoxy)-4-ethylsulfonyl benzoate viscous oil was sufficiently pure for the subsequent reactions.

Yield: 0.91 g (about 72% of theory)

¹H-NMR: δ [CDCl₃] 1.24 (t, 9H), 2.22 (s, 3H), 3.45 (q, 2H), 3.96 (s, 3H), 4.83 (s, 2H), 7.70 (d, 1H), 7.92 (d, 1H)

Step 3: 2-Chloro-3-(methylcarbonylmethoxy)-4-ethylsulfonylbenzoic acid 0.870 g (2.60 mmol) of methyl 2-chloro-3-(methylcarbonylmethoxy)-4-ethylsulfonyl-benzoate was dissolved in a mixture of 10 ml of THF and 10 ml of water, and 0.114 g (2.90 mmol) of NaOH was added. The mixture was stirred at RT for 12 h and then evaporated to dryness. The residue was taken up in water, 6 N HCl was added and the mixture was extracted with CH₂Cl₂. Drying with Na₂SO₄ and concentration of the organic phase gave 2-chloro-3-(methylcarbonylmethoxy)-4-ethylsulfonylbenzoic acid in the form of a colorless viscous oil.

Yield: 0.590 g (about 71% of theory)

¹H-NMR: δ [CDCl₃] 1.27 (m, 3H), 2.26 (s, 3H), 3.55 (q, 2H), 4.83 (s, 2H), 7.86 (d, 1H), 7.97 (d, 1H)

Step 4: 3-Oxo-1-cyclohexenyl 2-chloro-3-(methylcarbonylmethoxy)-4-ethylsulfonylbenzoate 0.295 g (0.9 mmol) of 2-chloro-3-(methylcarbonylmethoxy)-4-ethylsulfonylbenzoic acid, 0.113 g (1.0 mmol) of cyclohexane-1,3-dione, 0.180 g (0.9 mmol) of N'-(3-dimethylaminopropyl)-N-ethylcarbodiimide hydrochloride and 0.001 g of dimethyl-aminopyridine were stirred in 25 ml of CH₂Cl₂ at RT for 2 h. The mixture was then diluted with CH₂Cl₂ and washed with 0.5 N HCl, with water, with saturated NaHCO₃ solution and again with water. The combined organic phases were dried over Na₂SO₄ and then evaporated to dryness, giving 3-oxo-1-cyclohexenyl 2-chloro-3-(methylcarbonylmethoxy)-4-ethylsulfonylbenzoate in the form of a brown resin which was sufficiently pure for the subsequent reaction.

Yield: 0.320 g (about 68% of theory)

¹H-NMR: δ [CDCl₃] 1.27 (t, 3H), 2.14 (m, 2H), 2.24 (s, 3H), 2.49 (m, 2H), 2.70 (m, 2H), 3.17 (q, 2H), 3.57 (q, 2H), 4.81 (s, 2H), 6.07 (m, 1H), 7.81 (d, 1H), 7.99 (d, 1H)

Step 5: (2-Chloro-3-(methylcarbonylmethoxy)-4-ethylsulfonylbenzoyl)-cyclohexane-1,3-dione 0.290 g (about 0.70 mmol) of 3-oxo-1-cyclohexenyl 2-chloro-3-(methylcarbonylmethoxy)-4-ethylsulfonylbenzoate was dissolved in 10 ml of acetonitrile. 3 drops of acetone cyanohydrin and 0.120 g (1.20 mmol) of triethylamine were added. The mixture was stirred at room temperature for 3 h and then evaporated to dryness, the residue was taken up in water and 6 N hydrochloric acid was added to the mixture. The mixture was then extracted with CH₂Cl₂. The combined organic phases were dried over Na₂SO₄, evaporated to dryness and chromatographed on reversed-phase silica gel (mobile phase: acetonitrile/water gradient), giving 0.9 g of a product fraction which was contaminated with the corresponding ketone cyanohydrin. For cleaving the cyanohydrin, this product fraction was taken up in 1 ml of THF, 2 ml of 1 N NaOH were added and the mixture was stirred at 23° C. for 15 min. Th solution was acidified with 1 N HCl and extracted with CH₂Cl₂. Drying over Na₂SO₄ and evaporation of the organic phases to dryness gave (2-chloro-3-(methylcarbonylmethoxy)-4-ethyl-sulfonylbenzoyl)cyclohexane-1,3-dione in pure form as a viscous oil.

Yield: 0.87 mg (about 31% of theory) R$_f$ (ethyl acetate): 0.40 ¹H-NMR: δ [CDCl₃] 1.29 (t, 6H), 2.08 (m, 2H), 2.24 (s, 3H), 2.46 (m, 2H), 2.84 (m, 2H ), 3.51 (q, 2H), 4.81 (s, 2H), 7.09 (d, 1H), 7.92 (d, 1H)

b) Preparation of 2,4-dibromo-3-(ethylcarbonylmethoxy) cyclohexane-1,3-dione (tabulated example No. 3.5)

Step 1: 2,4-Dibromo-3-(ethylcarbonylmethoxy)benzoate 0.853 g (6.20 mmol) of K₂CO₃, 0.154 g (0.90 mmol) of KI and 1.000 g (3.10 mmol) of ethyl 2,4-dibromo-3-hydroxybenzoate were initially charged in 10 ml of DMF. At RT, 0.621 g (3.70 mmol) of 1-bromo-2-butanone was added, and the mixture was then heated at 80° C. for 4 h. The mixture was then poured into water and extracted with diisopropyl ether. The combined organic phases were washed with water, dried over Na₂SO₄ and evaporated to dryness. Drying under oil pump vacuum gave ethyl 2,4-dibromo-3-(ethylcarbonylmethoxy)benzoate as a brown oil.

Yield: 1.18 g (about 87% of theory)

¹H-NMR: δ [CDCl₃] 1.14 (t, 3H), 1.20 (t, 3H), 2.83 (q, 2H) 4.20 (q, 2H), 4.57 (s, 2H), 7.21 (d, 1H), 7.59 (d, 1H)

Step 2: 2,4-Dibromo-3-(ethylcarbonylmethoxy)benzoic acid 1.280 g (3.20 mmol) of ethyl 2,4-dibromo-3-(ethylcarbonylmethoxy)benzoate were dissolved in 15 ml of THF and 15 ml of water, and 0.143 g (3.6 mmol) of NaOH was added. The mixture was stirred at RT for 12 h and then evaporated to dryness. The residue was taken up in water, and 6 N HCl was added. The resulting precipitate was filtered off with suction and dried. This gave 2,4-dibromo-3-(ethylcarbonylmethoxy)benzoic acid in the form of a white solid.

Yield: 0.86 g (69% of theory)

¹H-NMR: [d6-DMSO] 1.00 (t, 3H), 2.65 (q, 2H), 4.66 (s, 2H), 7.43 (d, 1H), 7.77 (d, 1H)

Step 3: 3-Oxo-1-cyclohexenyl 2,4-dibromo-3-(ethylcarbonylmethoxy)benzoate 0.415 g (1.10 mmol) of 2,4-dibromo-3-(ethylcarbonylmethoxy)benzoic acid, 0.140 g (1.20 mmol) of cyclohexane-1,3-dione, 0.222 g (1.10 mmol) of N'-(3-dimethylaminopropyl)-N-ethylcarbodiimide hydrochloride and 0.001 g of dimethylaminopyridine were stirred in 30 ml of CH₂Cl₂ at room temperature for 3 h. The mixture was then diluted with CH₂Cl₂ and washed with 0.5 N HCl, with water, with saturated NaHCO₃ solution and again with water. The combined organic phases were dried over Na₂SO₄ and evaporated to dryness, giving 3-oxo-1-cyclohexenyl 2,4-dibromo-3-(ethylcarbonylmethoxy) benzoate in the form of a yellow resin which was sufficiently pure for the subsequent reaction.

Yield: 0.280 g

¹H-NMR: δ [CDCl₃] 1.18 (t, 3H), 2.13 (m, 2H), 2.47 (m, 2H), 2.70 (m, 2H), 2.83 (q, 2H), 4.57 (s, 2H), 6.04 (m,1H), 7.54 (d, 1H), 7.65 (d, 1H)

Step 4: 2,4-Dibromo-3-(ethylcarbonylmethoxy) cyclohexane-1,3-dione 0.280 g (about 0.60 mmol) of 3-oxo-1-cyclohexenyl 2,4-dibromo-3-(ethylcarbonylmethoxy)benzoate was dissolved in 5 ml of acetonitrile. 3 drops of acetone cyanohydrin, 0.012 g (0.2 mmol) of KCN and 0.105 g (1.00 mmol) of triethylamine were added. The mixture was stirred at RT for 4 h, and 0.005 g (0.10 mmol) of KCN was then added. After a further 10 h at RT, the mixture was evaporated to dryness, the residue was taken up in water and 6 N HCl was added to the mixture. The mixture was then extracted with CH₂Cl₂. The combined organic phases were dried over Na₂SO₄, evaporated to dryness and chromatographed on reversed-phase silica gel (mobile phase: acetonitrile/water gradient), giving 2,4-dibromo-3-(ethylcarbonylmethoxy)cyclohexane-1,3-dione in the form of a colorless viscous oil and a separate fraction of the corresponding ketone cyanohydrin which can be converted into the ketone according to example 1.1 (step 5).

Yield: 21 mg (about 7.5% of theory) and 22 mg (about 7.5% of theory) of ketone cyanohydrin $R_f$ (ethyl acetate): 0.29

$^1$H-NMR: δ [CDCl$_3$] 1.16 (t, 3H), 2.05 (m, 2H), 2.45 (m, 2H), 2.75–2.89 (m, 4H), 4.54 (s, 2H), 6.83 (d, 1H), 7.58 (d, 1H)

c) Preparation of (2,4-dibromo-3-(2-ethoxyiminopropyloxy)benzoyl)cyclohexane-1,3-dione Step 1: Ethyl 2,4-dibromo-3-(2-ethoxyiminopropyloxy) benzoate 1.00 g (2.60 mmol) of ethyl 2,4-dibromo-3-(methylcarbonylmethoxy)benzoate (prepared from ethyl 2,4-dibromo-3-hydroxybenzoate and chloroacetone analogously to preparation a), step 1, above) and 0.614 g (5.80 mmol) of Na$_2$CO$_3$ were initially charged in 10 ml of methanol. 0.529 g (5.30 mmol) of O-ethyl hydroxylamine hydrochloride, dissolved in 12 ml of water, was added dropwise and the mixture was stirred at RT for 2 h. The mixture was then poured into water and extracted with diethyl ether. The combined organic phases were washed with water, dried over Na$_2$SO$_4$ and evaporated to dryness. Drying under oil pump vacuum gave ethyl 2,4-dibromo-3-(2-ethoxyiminopropyloxy)benzoate as a brown oil.

Yield: 0.82 g (about 59% of theory)

$^1$H-NMR: δ [CDCl$_3$] 1.21&1.39 (2t, 3H), 1.20 (t, 3H), 2.16&2.22 (2s,3H), 4.04&4.13 (2t, 2H), 4.37 (q, 2H), 4.54&4.84 (2s, 2H), 7.36 (m, 1H), 7.57 (d, 1H)

Step 2: 2,4-Dibromo-3-(2-ethoxyiminopropyloxy) benzoic acid 0.820 g (1.90 mmol) of ethyl 2,4-dibromo-3-(2-ethoxyiminopropyloxy)benzoate was dissolved in a mixture of 8 ml of THF and 8 ml of water, and 0.085 g (2.10 mmol) of NaOH was added. The mixture was stirred at RT for 12 h and then evaporated to dryness. The residue was taken up in water, and 6 N HCl was added. The mixture was then extracted with methylene chloride. The organic phase was dried using Na$_2$SO$_4$ and concentrated, giving 2,4-dibromo-3-(2-ethoxyiminopropyloxy)benzoic acid in the form of a colorless viscous oil.

Yield: 0.59 g (about 65% of theory)

$^1$H-NMR: δ [CDCl$_3$] 1.22&1.37 (2t, 3H), 2.16&2.23 (2s, 3H), 4.08&4.18 (2q, 2H), 4.58&4.86 (2s, 2H), 7.6 (m, 2H)

Step 3: 3-Oxo-1-cyclohexenyl 2,4-dibromo-3-(2-ethoxyiminopropyloxy)-benzoate 0.280 g (0.70 mmol) of 2,4-dibromo-3-(2-ethoxyiminopropyloxy)benzoic acid, 0.087 g (0.80 mmol) of cyclohexane-1,3-dione, 0.139 g (0.70 mmol) of N'-(3-dimethylaminopropyl)-N-ethylcarbodiimide hydrochloride and 0.001 g of dimethylaminopyridine were stirred in 15 ml of CH$_2$Cl$_2$ at RT for 3 h. The mixture was then diluted with CH$_2$Cl$_2$ and washed with 0.5 N HCl, water, saturated NaHCO$_3$ solution and again with water. The combined organic phases were dried over Na$_2$SO$_4$ and evaporated to dryness, giving 3-oxo-1-cyclohexenyl 2,4-dibromo-3-(2-ethoxyiminopropyloxy)-benzoate in the form of a yellow resin of sufficient purity.

Yield: 0.320 g $^1$H-NMR: δ [CDCl$_3$] 1.27 (t, 3H), 2.13 (m, 5H), 2.45 (m, 2H), 2.66 (m, 2H), 4.07&4.15 (2q, 4H), 4.1&4.54 (2s, 2H), 6.04 (m, 1H), 7.49 (d, 1H), 7.64 (d, 1H)

Step 4: 2,4-dibromo-3-(2-ethoxyiminopropyloxy) cyclohexane-1,3-dione (tabulated example No. 6.31)

0.290 g (about 0.60 mmol) of 3-oxo-1-cyclohexenyl 2,4-dibromo-3-(2-ethoxyiminopropyloxy)benzoate was dissolved in 5 ml of acetonitrile. 3 drops of acetone cyanohydrin, 0.012 g (0.2 mmol) of KCN and 0.102 g (1.00 mmol) of NEt$_3$ were added. The mixture was stirred at RT for 2 h. The residue was then taken up in water, and 6 N HCl was added. The mixture was then extracted with CH$_2$Cl$_2$. Drying of the combined organic phases over Na$_2$SO$_4$, evaporation to dryness and chromatography on reversed-phase silica gel (mobile phase: acetonitrile/water gradient) gave 2,4-dibromo-3-(2-ethoxyiminopropyloxy) cyclohexane-1,3-dione in the form of a colorless oil.

Yield: 36 mg (11% of theory) $R_f$ (ethyl acetate): 0.44

$^1$H-NMR: δ [CDCl$_3$] 1.28 (t, 3H), 2.05 (m, 2H), 2.13&2.18 (2s, 3H), 2.43 (m, 2H), 2.78 (m, 2H), 4.14 (q, 2H), 4.54 (s, 2H), 6.80 (d, 1H), 7.76 (d, 1H)

d) Preparation of (2-chloro-3-(2-allyloxyiminopropyloxy)-4-ethylsulfonylbenzoyl)-cyclohexane-1,3-dione (tabulated example No. 6.25)

Step 1: Methyl 2-chloro-3-(2-allyloxyiminopropyloxy)-4-ethanesulfonylbenzoate 0.730 g (2.20 mmol) of methyl 2-chloro-3-hydroxy-4-ethylsulfonylbenzoate, 0.412 g (4.40 mmol) of O-allyl hydroxylamine hydrochloride and 0.508 g (4.80 mmol) of Na$_2$CO$_3$ were reacted analogously to preparation c).

Yield: 0.540 g (about 63% of theory)

$^1$H-NMR: δ [CDCl$_3$] 1.24&1.27 (2t, 3H), 2.11&2.15 (2s, 3H), 3.38&3.46 (2q, 2H), 3.97 (s, 3H), 4.38 (m, 1H), 4.63 (m, 1H), 4.76&5.08 (2s, 2H), 5.10 (m, 1H), 5.31 (m, 1H), 5.86–6.09 (m, 1H), 7.66 (m, 1H), 7.93 (d, 1H)

Step 2: 2-Chloro-3-(2-allyloxyiminopropyloxy)-4-ethanesulfonylbenzoic acid 0.540 g (about 1.40 mmol) of methyl 2-chloro-3-(2-allyloxyiminopropyloxy)-4-ethanesulfonylbenzoate and 0.061 g (1.50 mmol) of NaOH were reacted analogously to preparation c).

Yield: 0.526 g (about 100% of theory)

$^1$H-NMR: δ [CDCl$_3$] 1.27&1.28 (2t, 3H), 2.11&2.19 (2s, 3H), 3.20&3.47 (2q, 2H), 4.40 (m, 1H), 4.66 (m, 1H), 4.80&5.09 (2s, 2H), 5.10 (m, 1H), 5.31 (m, 1H), 5.85–6.09 (m, 1H), 7.84 (m, 1H), 7.97 (d, 1H)

Step 3: 3-Oxo-1-cyclohexenyl 2-chloro-3-(2-allyloxyiminopropyloxy)-4-ethanesulfonylbenzoate 0.526 g (1.40 mmol) of 2-chloro-3-(2-allyloxyiminopropyloxy)-4-ethanesulfonylbenzoic acid, 0.173 g (1.50 mmol) of cyclohexane-1,3-dione, 0.274 g (1.40 mmol) of N'-(3-dimethylaminopropyl)-N-ethylcarbodiimide hydrochloride and 0.002 g of dimethylaminopyridine were reacted analogously to preparation c).

Yield: 0.510 g $^1$H-NMR: δ [CDCl$_3$] 1.27&1.28 (2t, 3H), 2.13&2.20 (2s, 3H), 2.49 (m, 2H), 2.73 (m, 2H), 3.46&3.54 (2q, 2H), 4.51 (m, 1H), 4.65 (m, 1H), 4.76&5.08 (2s, 2H), 5.10 (m, 1H), 5.31 (m, 1H), 5.86–6.05 (m, 1H), 6.11 (s, 1H), 7.78 (m, 1H), 8.00 (d, 1H)

Step 4: 2-Chloro-3-(2-allyloxyiminopropyloxy)-4-ethylsulfonylcyclohexane-1,3-dione 0.510 g (about 1.10 mmol) of 3-oxo-1-cyclohexenyl 2-chloro-3-(2-allyloxyiminopropyloxy)-4-ethanesulfonylbenzoate, 3 drops of acetone cyanohydrin, 0.022 g (0.3 mmol) of KCN and 0.187 g (1.80 mmol) of NEt$_3$ were reacted analogously to preparation c). Chromatography on reversed-phase silica gel (mobile phase: acetonitrile/water gradient) gave 2-chloro-3-(2-allyloxyiminopropyloxy)-4-ethanesulfonylcyclohexane-1, 3-dione in the form of a colorless oil.

Yield: 218 mg (about 40% of theory) $R_f$ (ethyl acetate): 0.15

$^1$H-NMR: δ [CDCl$_3$] 1.2 (t, 3H), 2.01–2.12 (m, 3H), 2.45 (m, 2H), 2.81 (m, 2H), 3.39&3.43 (2q, 2H), 4.51 (m, 1H), 4.62 (m, 1 H), 4.76&5.07 (2s, 2H), 5.10 (m, 1H), 5.30 (m, 1H), 5.87–6.08 (m, 1H), 7.11 (d, 1H), 7.93 (m, 1H)

The examples given in the tables which follow were prepared analogously to abovementioned methods, or can be prepared analogously to the abovementioned methods.

The abbreviations used herein denote:

| | | | |
|---|---|---|---|
| Bu = butyl | Et = ethyl | Me = methyl | Pr = propyl |
| c = cyclo | i = iso | t = tertiary | m.p. = melting point |
| EA = ethyl acetate | $R_f$ = retention value | Ph = phenyl | |

TABLE 1

Compounds according to the invention of the formula (I) in which the substituents and symbols have the following meanings:
$R^{1a}$ = Cl   $R^{1b}$ = $SO_2$Me   $R^{1c}$ = H
$R^4$ = OH   $X^3$ = O   Y = $CH_2$
Z = $CH_2$

| No. | $X^1$–$X^2$ | $R^2$ | $R^5$ | Physical data |
|---|---|---|---|---|
| 1.1 | —$OCH_2$— | H | H | |
| 1.2 | —$OCH_2$— | Me | H | $R_f$ (EA): 0.16 |
| 1.3 | —$OCH_2$— | Me | Me | |
| 1.4 | —$OCH_2$— | Et | H | $R_f$ (EA): 0.16 |
| 1.5 | —$OCH_2$— | n-Pr | H | |
| 1.6 | —$OCH_2$— | i-Pr | H | $R_f$ (EA): 0.16 |
| 1.7 | —$OCH_2$— | n-Bu | H | $R_f$ (EA): 0.16 |
| 1.8 | —$OCH_2$— | t-Bu | Me | $R_f$ (EA): 0.29 |
| 1.9 | —$OCH_2$— | t-Bu | H | $R_f$ (EA): 0.23 |
| 1.10 | —$OCH_2$— | $CH(CH_3)CH_2CH_3$ | H | |
| 1.11 | —$OCH_2$— | $CH_2CH(CH_3)CH_3$ | H | $R_f$ (EA): 0.18 |
| 1.12 | —$OCH_2$— | n-pentyl | H | |
| 1.13 | —$OCH_2$— | $CH_2CH_2CH(CH_3)CH_3$ | H | |
| 1.14 | —$OCH_2$— | CH=$CH_2$ | H | |
| 1.15 | —$OCH_2$— | $CH_2$CH=$CH_2$ | H | |
| 1.16 | —$OCH_2$— | C≡CH | H | |
| 1.17 | —$OCH_2$— | CHC≡CH | H | |
| 1.18 | —$OCH_2$— | $CH_2CH_2$Cl | H | |
| 1.19 | —$OCH_2$— | c-Pr | H | $R_f$ (EA): 0.13 |
| 1.20 | —$OCH_2$— | c-Bu | H | |
| 1.21 | —$OCH_2$— | c-pentyl | H | |
| 1.22 | —$OCH_2$— | c-hexyl | H | |
| 1.23 | —$OCH_2$— | 2,2-dichlorocyclopropyl | H | |
| 1.24 | —$OCH_2$— | 2,2-difluorocyclopropyl | H | |
| 1.25 | —$OCH_2$— | 1-cyclopentenyl | H | |
| 1.26 | —$OCH_2$— | Ph | H | |
| 1.27 | —$OCH_2$— | 4-methylphenyl | H | |
| 1.28 | —$OCH_2$— | 2-chlorophenyl | H | |
| 1.29 | —$OCH_2$— | benzyl | H | |
| 1.30 | —$OCH_2$— | 2-chlorobenzyl | H | |
| 1.31 | —$OCH_2$— | 3-methyl-5-isoxazolinyl | H | |
| 1.32 | —$OCH_2$— | 3-methyl-5-isoxazolyl | H | |
| 1.33 | —$OCH_2$— | (3-methyl-5-isoxazolinyl)methyl | H | |
| 1.34 | —$OCH_2CH_2$— | (3-methyl-5-isoxazolyl)methyl | H | |
| 1.35 | —$OCH_2CH_2$— | H | H | |
| 1.36 | —$OCH_2CH_2$— | Me | H | |
| 1.37 | —$OCH_2CH_2$— | Me | Me | |
| 1.38 | —$OCH_2CH_2$— | Et | H | |

TABLE 1-continued

Compounds according to the invention of the formula (I) in which the substituents and symbols have the following meanings:
$R^{1a}$ = Cl   $R^{1b}$ = $SO_2$Me   $R^{1c}$ = H
$R^4$ = OH   $X^3$ = O   Y = $CH_2$
Z = $CH_2$

| No. | $X^1$–$X^2$ | $R^2$ | $R^5$ | Physical data |
|---|---|---|---|---|
| 1.39 | —$OCH_2CH_2$— | n-Pr | H | |
| 1.40 | —$OCH_2CH_2$— | i-Pr | H | |
| 1.41 | —$OCH_2CH_2$— | n-Bu | H | |
| 1.42 | —$OCH_2CH_2$— | n-Bu | Me | |
| 1.43 | —$OCH_2CH_2$— | t-Bu | H | |
| 1.44 | —$OCH_2CH_2$— | $CH(CH_3)CH_2CH_3$ | H | |
| 1.45 | —$OCH_2CH_2$— | $CH_2CH(CH_3)CH_3$ | H | |
| 1.46 | —$OCH_2CH_2$— | n-pentyl | H | |
| 1.47 | —$OCH_2CH_2$— | $CH_2CH_2CH(CH_3)CH_3$ | H | |
| 1.48 | —$OCH_2CH_2$— | CH=$CH_2$ | H | |
| 1.49 | —$OCH_2CH_2$— | $CH_2$CH=$CH_2$ | H | |
| 1.50 | —$OCH_2CH_2$— | C≡CH | H | |
| 1.51 | —$OCH_2CH_2$— | CHC≡CH | H | |
| 1.52 | —$OCH_2CH_2$— | $CH_2CH_2$Cl | H | |
| 1.53 | —$OCH_2CH_2$— | c-Pr | H | |
| 1.54 | —$OCH_2CH_2$— | c-Bu | H | |
| 1.55 | —$OCH_2CH_2$— | c-pentyl | H | |
| 1.56 | —$OCH_2CH_2$— | c-hexyl | H | |
| 1.57 | —$OCH_2CH_2$— | 2,2-dichlorocyclopropyl | H | |
| 1.58 | —$OCH_2CH_2$— | 2,2-difluorocyclopropyl | H | |
| 1.59 | —$OCH_2CH_2$— | 1-cylcopentenyl | H | |
| 1.60 | —$OCH_2CH_2$— | Ph | H | |
| 1.61 | —$OCH_2CH_2$— | 4-methylphenyl | H | |
| 1.62 | —$OCH_2CH_2$— | 2-chlorophenyl | H | |
| 1.63 | —$OCH_2CH_2$— | benzyl | H | |
| 1.64 | —$OCH_2CH_2$— | 2-chlorobenzyl | H | |
| 1.65 | —$OCH_2CH_2$— | 3-methyl-5-isoxazolinyl | H | |
| 1.66 | —$OCH_2CH_2$— | 3-methyl-5-isoxazolyl | H | |
| 1.67 | —$OCH_2CH_2$— | (3-methyl-5-isoxazolinyl)methyl | H | |
| 1.68 | —$OCH_2CH_2$— | (3-methyl-5-isoxazolyl)methyl | H | |
| 1.69 | —$OCH_2$CH=CH— | H | H | |
| 1.70 | —$OCH_2$CH=CH— | Me | H | |
| 1.71 | —$OCH_2$CH=CH— | Me | Me | |
| 1.72 | —$OCH_2$CH=CH— | Et | H | |
| 1.73 | —$OCH_2$CH=CH— | n-Pr | H | |
| 1.74 | —$OCH_2$CH=CH— | i-Pr | H | |
| 1.75 | —$OCH_2$CH=CH— | n-Bu | H | |
| 1.76 | —$OCH_2$CH=CH— | n-Bu | Me | |
| 1.77 | —$OCH_2$CH=CH— | t-Bu | H | |
| 1.78 | —$OCH_2$CH=CH— | $CH(CH_3)CH_2CH_3$ | H | |
| 1.79 | —$OCH_2$CH=CH— | $CH_2CH(CH_3)CH_3$ | H | |
| 1.80 | —$OCH_2$CH=CH— | n-pentyl | H | |
| 1.81 | —$OCH_2$CH=CH— | $CH_2CH_2CH(CH_3)CH_3$ | H | |
| 1.82 | —$OCH_2$CH=CH— | CH=$CH_2$ | H | |
| 1.83 | —$OCH_2$CH=CH— | $CH_2$CH=$CH_2$ | H | |
| 1.84 | —$OCH_2$CH=CH— | C≡CH | H | |
| 1.85 | —$OCH_2$CH=CH— | CHC≡CH | H | |
| 1.86 | —$OCH_2$CH=CH— | $CH_2CH_2$Cl | H | |
| 1.87 | —$OCH_2$CH=CH— | c-Pr | H | |
| 1.88 | —$OCH_2$CH=CH— | c-Bu | H | |
| 1.89 | —$OCH_2$CH=CH— | c-pentyl | H | |
| 1.90 | —$OCH_2$CH=CH— | c-hexyl | H | |
| 1.91 | —$OCH_2$CH=CH— | 2,2-dichlorocyclopropyl | H | |
| 1.92 | —$OCH_2$CH=CH— | 2,2-difluorocyclopropyl | H | |
| 1.93 | —$OCH_2$CH=CH— | 1-cyclopentenyl | H | |
| 1.94 | —$OCH_2$CH=CH— | Ph | H | |
| 1.95 | —$OCH_2$CH=CH— | 4-methylphenyl | H | |
| 1.96 | —$OCH_2$CH=CH— | 2-chlorophenyl | H | |
| 1.97 | —$OCH_2$CH=CH— | benzyl | H | |
| 1.98 | —$OCH_2$CH=CH— | 2-chlorobenzyl | H | |

TABLE 1-continued

Compounds according to the invention of the formula (I) in which the substituents and symbols have the following meanings:
$R^{1a}$ = Cl $\quad$ $R^{1b}$ = SO$_2$Me $\quad$ $R^{1c}$ = H
$R^4$ = OH $\quad$ $X^3$ = O $\quad$ Y = CH$_2$
Z = CH$_2$

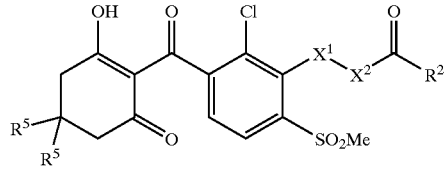

| No. | $X^1$–$X^2$ | $R^2$ | $R^5$ | Physical data |
|---|---|---|---|---|
| 1.99 | —OCH$_2$CH=CH— | 3-methyl-5-isoxazolinyl | H | |
| 1.100 | —OCH$_2$CH=CH— | 3-methyl-5-isoxazolyl | H | |
| 1.101 | —OCH$_2$CH=CH— | (3-methyl-5-isoxazolinyl)methyl | H | |
| 1.102 | —OCH$_2$CH=CH— | (3-methyl-5-isoxazolyl)methyl | H | |
| 1.103 | —OCH$_2$C≡C— | H | H | |
| 1.104 | —OCH$_2$C≡C— | Me | H | |
| 1.105 | —OCH$_2$C≡C— | Me | Me | |
| 1.106 | —OCH$_2$C≡C— | Et | H | |
| 1.107 | —OCH$_2$C≡C— | n-Pr | H | |
| 1.108 | —OCH$_2$C≡C— | i-Pr | H | |
| 1.109 | —OCH$_2$C≡C— | n-Bu | H | |
| 1.110 | —OCH$_2$C≡C— | n-Bu | Me | |
| 1.111 | —OCH$_2$C≡C— | t-Bu | H | |
| 1.112 | —OCH$_2$C≡C— | CH(CH$_3$)CH$_2$CH$_3$ | H | |
| 1.113 | —OCH$_2$C≡C— | CH$_2$CH(CH$_3$)CH$_3$ | H | |
| 1.114 | —OCH$_2$C≡C— | n-pentyl | H | |
| 1.115 | —OCH$_2$C≡C— | CH$_2$CH$_2$CH(CH$_3$)CH$_3$ | H | |
| 1.116 | —OCH$_2$C≡C— | CH=CH$_2$ | H | |
| 1.117 | —OCH$_2$C≡C— | CH$_2$CH=CH$_2$ | H | |
| 1.118 | —OCH$_2$C≡C— | C≡CH | H | |
| 1.119 | —OCH$_2$C≡C— | CHC≡CH | H | |
| 1.120 | —OCH$_2$C≡C— | CH$_2$CH$_2$Cl | H | |
| 1.121 | —OCH$_2$C≡C— | c-Pr | H | |
| 1.122 | —OCH$_2$C≡C— | c-Bu | H | |
| 1.123 | —OCH$_2$C≡C— | c-pentyl | H | |
| 1.124 | —OCH$_2$C≡C— | c-hexyl | H | |
| 1.125 | —OCH$_2$C≡C— | 2,2-dichlorocyclopropyl | H | |
| 1.126 | —OCH$_2$C≡C— | 2,2-difluorocyclopropyl | H | |
| 1.127 | —OCH$_2$C≡C— | 1-cyclopentenyl | H | |
| 1.128 | —OCH$_2$C≡C— | Ph | H | |
| 1.129 | —OCH$_2$C≡C— | 4-methylphenyl | H | |
| 1.130 | —OCH$_2$C≡C— | 2-chlorophenyl | H | |
| 1.131 | —OCH$_2$C≡C— | benzyl | H | |
| 1.132 | —OCH$_2$C≡C— | 2-chlorobenzyl | H | |
| 1.133 | —OCH$_2$C≡C— | 3-methyl-5-isoxazolinyl | H | |
| 1.134 | —OCH$_2$C≡C— | 3-methyl-5-isoxazolyl | H | |
| 1.135 | —OCH$_2$C≡C— | (3-methyl-5-isoxazolinyl)methyl | H | |
| 1.136 | —OCH$_2$C≡C— | (3-methyl-5-isoxazolyl)methyl | H | |

TABLE 2

Compounds according to the invention of formula (I) in which the substituents and symbols have the following meanings:
$R^{1a}$ = Cl $\quad$ $R^{1b}$ = SO$_2$Me $\quad$ $R^{1c}$ = H
$X^3$ = O $\quad$ Y = CH$_2$ $\quad$ Z = CH$_2$

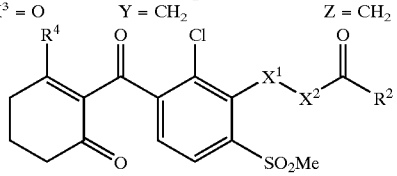

| No. | $X^1$–$X^2$ | $R^2$ | $R^4$ | Physical data |
|---|---|---|---|---|
| 2.1 | —OCH$_2$— | Me | O—Ph | |
| 2.2 | —OCH$_2$— | Me | S-allyl | |
| 2.3 | —OCH$_2$— | Et | O—Et | |
| 2.4 | —OCH$_2$— | Et | O—Ph | |
| 2.5 | —OCH$_2$— | i-Pr | S-allyl | |
| 2.6 | —OCH$_2$— | n-Bu | O—Ph | |
| 2.7 | —OCH$_2$— | t-Bu | S-allyl | |
| 2.8 | —OCH$_2$— | CH(CH$_3$)CH$_2$CH$_3$ | O—Ph | |
| 2.9 | —OCH$_2$— | CH$_2$CH(CH$_3$)CH$_3$ | S-allyl | |
| 2.10 | —OCH$_2$— | n-pentyl | O—Et | |
| 2.11 | —OCH$_2$— | CH$_2$CH$_2$CH(CH$_3$)CH$_3$ | S-allyl | |
| 2.12 | —OCH$_2$— | CH=CH$_2$ | O—Ph | |
| 2.13 | —OCH$_2$— | c-Pr | S—Ph | |
| 2.14 | —OCH$_2$— | 2,2-difluorocyclopropyl | O—Et | |
| 2.15 | —OCH$_2$— | Ph | O—Ph | |
| 2.16 | —OCH$_2$— | 2-chlorophenyl | S—Ph | |
| 2.17 | —OCH$_2$— | benzyl | S-allyl | |
| 2.18 | —OCH$_2$CH$_2$— | Me | S-allyl | |
| 2.19 | —OCH$_2$CH$_2$— | Et | O—Ph | |
| 2.20 | —OCH$_2$CH$_2$— | i-Pr | S-allyl | |
| 2.21 | —OCH$_2$CH$_2$— | t-Bu | S-allyl | |
| 2.22 | —OCH$_2$CH$_2$— | CH=CH$_2$ | O—Ph | |
| 2.23 | —OCH$_2$CH$_2$— | c-Pr | S—Ph | |
| 2.24 | —OCH$_2$CH=CH— | Me | S-allyl | |
| 2.25 | —OCH$_2$CH=CH— | Et | O—Ph | |
| 2.26 | —OCH$_2$CH=CH— | i-Pr | S-allyl | |
| 2.27 | —OCH$_2$CH=CH— | t-Bu | S-allyl | |
| 2.28 | —OCH$_2$CH=CH— | CH=CH$_2$ | O—Ph | |
| 2.29 | —OCH$_2$CH=CH— | c-Pr | S—Ph | |
| 2.30 | —OCH$_2$C≡C— | Me | S-allyl | |
| 2.31 | —OCH$_2$C≡C— | Et | O—Ph | |
| 2.32 | —OCH$_2$C≡C— | i-Pr | S-allyl | |
| 2.33 | —OCH$_2$C≡C— | t-Bu | S-allyl | |
| 2.34 | —OCH$_2$C≡C— | CH=CH$_2$ | O—Ph | |
| 2.35 | —OCH$_2$C≡C— | c-Pr | S—Ph | |

TABLE 3

Compounds according to the invention of the formula (I) in which the substituents and symbols have the following meanings:
$R^{1c}$ = H $\quad$ $X^3$ = O $\quad$ $R^4$ = OH
Y = CH$_2$ $\quad$ Y = CH$_2$ $\quad$ Z = CH$_2$

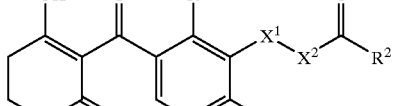

| No. | $R^{1a}$ | $R^{1b}$ | $X^1$–$X^2$ | $R^2$ | Physical data |
|---|---|---|---|---|---|
| 3.1 | Cl | Cl | OCH$_2$ | Me | $R_f$ (EA): 0.25 |
| 3.2 | Br | Br | OCH$_2$ | Me | |
| 3.3 | Cl | SO$_2$Et | OCH$_2$ | Me | $R_f$ (EA): 0.40 |
| 3.4 | Me | Br | OCH$_2$ | Et | $R_f$ (EA): 0.26 |
| 3.5 | Br | Br | OCH$_2$ | Et | $R_f$ (EA): 0.29 |
| 3.6 | Cl | SO$_2$Et | OCH$_2$ | Et | $R_f$ (EA): 0.14 |
| 3.7 | Cl | Cl | OCH$_2$ | i-Pr | $R_f$ (EA): 0.31 |
| 3.8 | Br | Br | OCH$_2$ | i-Pr | $R_f$ (EA): 0.23 |
| 3.9 | Cl | SO$_2$Et | OCH$_2$ | i-Pr | $R_f$ (EA): 0.16 |

TABLE 3-continued

Compounds according to the invention of the formula (I) in which the substituents and symbols have the following meanings:
$R^{1c}$ = H   $X^3$ = O   $R^4$ = OH
Y = $CH_2$   Y = $CH_2$   Z = $CH_2$

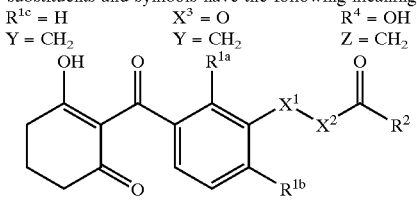

| No. | $R^{1a}$ | $R^{1b}$ | $X^1-X^2$ | $R^2$ | Physical data |
|---|---|---|---|---|---|
| 3.10 | Cl | Cl | $OCH_2$ | t-Bu | $R_f$ (EA): 0.30 |
| 3.11 | Cl | $SO_2Et$ | $OCH_2$ | t-Bu | $R_f$ (EA): 0.26 |
| 3.12 | Me | $SO_2Me$ | $OCH_2$ | t-Bu | $R_f$ (EA): 0.16 |
| 3.13 | Cl | Cl | $OCH_2$ | c-Pr | $R_f$ (EA): 0.21 |
| 3.14 | Br | Br | $OCH_2$ | c-Pr | $R_f$ (EA): 0.28 |
| 3.15 | Cl | $SO_2Et$ | $OCH_2$ | c-Pr | $R_f$ (EA): 0.11 |
| 3.16 | Cl | Cl | $OCH_2CH_2$ | Me | |
| 3.17 | Cl | $SO_2Et$ | $OCH_2CH_2$ | Me | |
| 3.18 | Cl | Cl | $OCH_2CH_2$ | Et | |
| 3.19 | Br | Br | $OCH_2CH_2$ | Et | |
| 3.20 | Cl | $SO_2Et$ | $OCH_2CH_2$ | Et | |
| 3.21 | Cl | Cl | $OCH_2CH_2$ | i-Pr | |
| 3.22 | Br | Br | $OCH_2CH_2$ | i-Pr | |
| 3.23 | Cl | Cl | $OCH_2CH_2$ | t-Bu | |
| 3.24 | Cl | $SO_2Et$ | $OCH_2CH_2$ | t-Bu | |
| 3.25 | Cl | $SO_2Et$ | $OCH_2CH_2$ | c-Pr | |
| 3.26 | Cl | Cl | $OCH_2CH=CH$ | Me | |
| 3.27 | Cl | $SO_2Et$ | $OCH_2CH=CH$ | Me | |
| 3.28 | Cl | Cl | $OCH_2CH=CH$ | Et | |
| 3.29 | Br | Br | $OCH_2CH=CH$ | Et | |
| 3.30 | Cl | $SO_2Et$ | $OCH_2CH=CH$ | Et | |
| 3.31 | Cl | Cl | $OCH_2CH=CH$ | i-Pr | |
| 3.32 | Br | Br | $OCH_2CH=CH$ | i-Pr | |
| 3.33 | Cl | Cl | $OCH_2CH=CH$ | t-Bu | |
| 3.34 | Cl | $SO_2Et$ | $OCH_2CH=CH$ | t-Bu | |
| 3.35 | Cl | $SO_2Et$ | $OCH_2CH=CH$ | c-Pr | |
| 3.36 | Cl | Cl | $OCH_2C\equiv C$ | Me | |
| 3.37 | Cl | $SO_2Et$ | $OCH_2C\equiv C$ | Me | |
| 3.38 | Cl | Cl | $OCH_2C\equiv C$ | Et | |
| 3.39 | Br | Br | $OCH_2C\equiv C$ | Et | |
| 3.40 | Cl | $SO_2Et$ | $OCH_2C\equiv C$ | Et | |
| 3.41 | Cl | Cl | $OCH_2C\equiv C$ | i-Pr | |
| 3.42 | Br | Br | $OCH_2C\equiv C$ | i-Pr | |
| 3.43 | Cl | Cl | $OCH_2C\equiv C$ | t-Bu | |
| 3.44 | Cl | $SO_2Et$ | $OCH_2C\equiv C$ | t-Bu | |
| 3.45 | Cl | $SO_2Et$ | $OCH_2C\equiv C$ | cyclopropyl | |
| 3.46 | Me | Br | $OCH_2$ | t-Bu | $R_f$ (EA): 0.21 |
| 3.47 | Cl | Cl | $OCH_2$ | $CH_2CH(CH_3)CH_3$ | $R_f$ (EA): 0.33 |
| 3.48 | Cl | $SO_2Et$ | $OCH_2$ | $CH_2CH(CH_3)CH_3$ | $R_f$ (EA): 0.18 |
| 3.49 | Cl | Cl | $OCH_2$ | Et | $R_f$ (EA): 0.29 |

TABLE 4

Compounds according to the invention of the formula (I) in which the substituents and symbols have the following meanings:
$R^{1a}$ = Cl   $R^{1b}$ = $SO_2Me$   $R^{1c}$ = H
$R^4$ = OH   $X^3$ = $ONR^3$   Y = $CH_2$
Z = $CH_2$

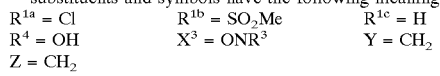
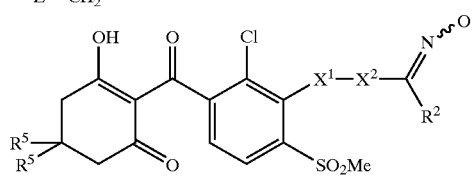

| No. | $X^1-X^2$ | $R^2$ | $R^3$ | $R^5$ | Physical data |
|---|---|---|---|---|---|
| 4.1 | $OCH_2$ | H | H | H | |
| 4.2 | $OCH_2$ | H | Me | H | |
| 4.3 | $OCH_2$ | H | Me | Me | |

TABLE 4-continued

Compounds according to the invention of the formula (I) in which the substituents and symbols have the following meanings:
$R^{1a}$ = Cl   $R^{1b}$ = $SO_2Me$   $R^{1c}$ = H
$R^4$ = OH   $X^3$ = $ONR^3$   Y = $CH_2$
Z = $CH_2$

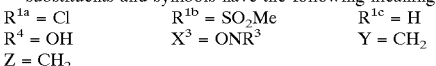
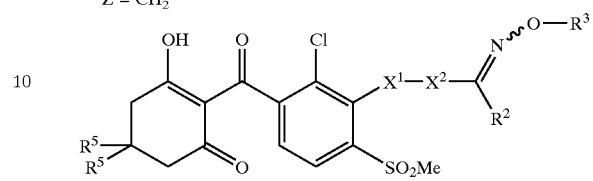

| No. | $X^1-X^2$ | $R^2$ | $R^3$ | $R^5$ | Physical data |
|---|---|---|---|---|---|
| 4.4 | $OCH_2$ | H | Et | H | |
| 4.5 | $OCH_2$ | H | Et | Me | |
| 4.6 | $OCH_2$ | H | n-Pr | H | |
| 4.7 | $OCH_2$ | H | 3-allyl | H | |
| 4.8 | $OCH_2$ | H | c-propylmethyl | H | |
| 4.9 | $OCH_2$ | H | Ph | H | |
| 4.10 | $OCH_2$ | H | benzyl | H | |
| 4.11 | $OCH_2$ | H | benzyl | Me | $R_f$ (EA): 0.11 |
| 4.12 | $OCH_2$ | H | 3-chlorobenzyl | H | |
| 4.13 | $OCH_2$ | Me | H | H | |
| 4.14 | $OCH_2$ | Me | Me | H | $R_f$ (EA): 0.11 |
| 4.15 | $OCH_2$ | Me | Me | Me | |
| 4.16 | $OCH_2$ | Me | Et | H | $R_f$ (EA): 0.11 |
| 4.17 | $OCH_2$ | Me | Et | Me | |
| 4.18 | $OCH_2$ | Me | n-Pr | H | |
| 4.19 | $OCH_2$ | Me | 3-allyl | H | $R_f$ (EA): 0.14 |
| 4.20 | $OCH_2$ | Me | c-propylmethyl | H | |
| 4.21 | $OCH_2$ | Me | Ph | H | |
| 4.22 | $OCH_2$ | Me | benzyl | H | |
| 4.23 | $OCH_2$ | Me | benzyl | Me | |
| 4.24 | $OCH_2$ | Me | 3-chlorobenzyl | H | |
| 4.25 | $OCH_2CH_2$ | H | H | H | |
| 4.26 | $OCH_2CH_2$ | H | Me | H | |
| 4.27 | $OCH_2CH_2$ | H | Me | Me | |
| 4.28 | $OCH_2CH_2$ | H | Et | H | |
| 4.29 | $OCH_2CH_2$ | H | Et | Me | |
| 4.30 | $OCH_2CH_2$ | H | n-Pr | H | |
| 4.31 | $OCH_2CH_2$ | H | 3-allyl | H | |
| 4.32 | $OCH_2CH_2$ | H | c-propylmethyl | H | |
| 4.33 | $OCH_2CH_2$ | H | Ph | H | |
| 4.34 | $OCH_2CH_2$ | H | benzyl | H | |
| 4.35 | $OCH_2CH_2$ | H | benzyl | Me | |
| 4.36 | $OCH_2CH_2$ | H | 3-chlorobenzyl | H | |
| 4.37 | $OCH_2CH_2$ | Me | H | H | |
| 4.38 | $OCH_2CH_2$ | Me | Me | H | |
| 4.39 | $OCH_2CH_2$ | Me | Me | Me | |
| 4.40 | $OCH_2CH_2$ | Me | Et | H | |
| 4.41 | $OCH_2CH_2$ | Me | Et | Me | |
| 4.42 | $OCH_2CH_2$ | Me | n-Pr | H | |
| 4.43 | $OCH_2CH_2$ | Me | 3-allyl | H | |
| 4.44 | $OCH_2CH_2$ | Me | c-propylmethyl | H | |
| 4.45 | $OCH_2CH_2$ | Me | Ph | H | |
| 4.46 | $OCH_2CH_2$ | Me | benzyl | H | |
| 4.47 | $OCH_2CH_2$ | Me | benzyl | Me | |
| 4.48 | $OCH_2CH_2$ | Me | 3-chlorobenzyl | H | |
| 4.49 | $OCH_2CH=CH$ | H | H | H | |
| 4.50 | $OCH_2CH=CH$ | H | Me | H | |
| 4.51 | $OCH_2CH=CH$ | H | Me | Me | |
| 4.52 | $OCH_2CH=CH$ | H | Et | H | |
| 4.53 | $OCH_2CH=CH$ | H | Et | Me | |
| 4.54 | $OCH_2CH=CH$ | H | n-Pr | H | |
| 4.55 | $OCH_2CH=CH$ | H | 3-allyl | H | |
| 4.56 | $OCH_2CH=CH$ | H | c-propylmethyl | H | |
| 4.57 | $OCH_2CH=CH$ | H | Ph | H | |
| 4.58 | $OCH_2CH=CH$ | H | benzyl | H | |
| 4.59 | $OCH_2CH=CH$ | H | benzyl | Me | |
| 4.60 | $OCH_2CH=CH$ | H | 3-chlorobenzyl | H | |
| 4.61 | $OCH_2CH=CH$ | Me | H | H | |
| 4.62 | $OCH_2CH=CH$ | Me | Me | H | |
| 4.63 | $OCH_2CH=CH$ | Me | Me | Me | |
| 4.64 | $OCH_2CH=CH$ | Me | Et | H | |
| 4.65 | $OCH_2CH=CH$ | Me | Et | Me | |

TABLE 4-continued

Compounds according to the invention of the formula (I) in which the substituents and symbols have the following meanings:
$R^{1a}$ = Cl   $R^{1b}$ = SO$_2$Me   $R^{1c}$ = H
$R^4$ = OH   $X^3$ = ONR$^3$   Y = CH$_2$
Z = CH$_2$

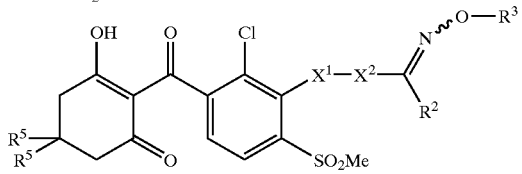

| No. | X$^1$–X$^2$ | R$^2$ | R$^3$ | R$^5$ | Physical data |
|---|---|---|---|---|---|
| 4.66 | OCH$_2$CH=CH | Me | n-Pr | H | |
| 4.67 | OCH$_2$CH=CH | Me | 3-allyl | H | |
| 4.68 | OCH$_2$CH=CH | Me | c-propylmethyl | H | |
| 4.69 | OCH$_2$CH=CH | Me | Ph | H | |
| 4.70 | OCH$_2$CH=CH | Me | benzyl | H | |
| 4.71 | OCH$_2$CH=CH | Me | benzyl | Me | |
| 4.72 | OCH$_2$CH=CH | Me | 3-chlorobenzyl | H | |
| 4.73 | OCH$_2$C≡C | H | H | H | |
| 4.74 | OCH$_2$C≡C | H | Me | H | |
| 4.75 | OCH$_2$C≡C | H | Me | Me | |
| 4.76 | OCH$_2$C≡C | H | Et | H | |
| 4.77 | OCH$_2$C≡C | H | Et | Me | |
| 4.78 | OCH$_2$C≡C | H | n-Pr | H | |
| 4.79 | OCH$_2$C≡C | H | 3-allyl | H | |
| 4.80 | OCH$_2$C≡C | H | c-propylmethyl | H | |
| 4.81 | OCH$_2$C≡C | H | Ph | H | |
| 4.82 | OCH$_2$C≡C | H | benzyl | H | |
| 4.83 | OCH$_2$C≡C | H | benzyl | Me | |
| 4.84 | OCH$_2$C≡C | H | 3-chlorobenzyl | H | |
| 4.85 | OCH$_2$C≡C | Me | H | H | |
| 4.86 | OCH$_2$C≡C | Me | Me | H | |
| 4.87 | OCH$_2$C≡C | Me | Me | Me | |
| 4.88 | OCH$_2$C≡C | Me | Et | H | |
| 4.89 | OCH$_2$C≡C | Me | Et | Me | |
| 4.90 | OCH$_2$C≡C | Me | n-Pr | H | |
| 4.91 | OCH$_2$C≡C | Me | 3-allyl | H | |
| 4.92 | OCH$_2$C≡C | Me | c-propylmethyl | H | |
| 4.93 | OCH$_2$C≡C | Me | Ph | H | |
| 4.94 | OCH$_2$C≡C | Me | benzyl | H | |
| 4.95 | OCH$_2$C≡C | Me | benzyl | Me | |
| 4.96 | OCH$_2$C≡C | Me | 3-chlorobenzyl | H | |
| 4.97 | OCH$_2$ | Et | Me | H | R$_f$ (EA): 0.15 |
| 4.98 | OCH$_2$ | Et | Et | H | R$_f$ (EA): 0.19 |
| 4.99 | OCH$_2$ | Et | 3-allyl | H | R$_f$ (EA): 0.19 |
| 4.100 | OCH$_2$ | Et | benzyl | H | R$_f$ (EA): 0.20 |

TABLE 5

Compounds according to the invention of the formula (I) in which the substituents and symbols have the following meanings:
$R^{1a}$ = Cl   $R^{1b}$ = SO$_2$Me   $R^{1c}$ = H
$R^5$ = H   $X^3$ = NOR$^3$   Y = CH$_2$
Z = CH$_2$

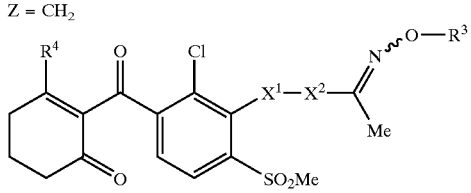

| No. | X$^1$–X$^2$ | R$^3$ | R$^4$ | Physical data |
|---|---|---|---|---|
| 5.1 | OCH$_2$ | Me | O—Ph | |
| 5.2 | OCH$_2$ | Me | S-allyl | R$_f$ (EA): |
| 5.3 | OCH$_2$ | Et | O—Et | |
| 5.4 | OCH$_2$ | Et | O—Ph | |
| 5.5 | OCH$_2$ | n-Pr | S-allyl | |
| 5.6 | OCH$_2$ | 3-allyl | O—Ph | |

TABLE 5-continued

Compounds according to the invention of the formula (I) in which the substituents and symbols have the following meanings:
$R^{1a}$ = Cl   $R^{1b}$ = SO$_2$Me   $R^{1c}$ = H
$R^5$ = H   $X^3$ = NOR$^3$   Y = CH$_2$
Z = CH$_2$

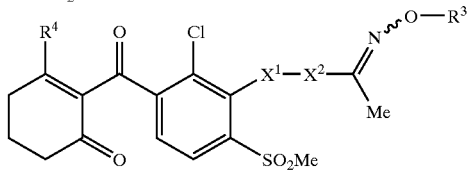

| No. | X$^1$–X$^2$ | R$^3$ | R$^4$ | Physical data |
|---|---|---|---|---|
| 5.7 | OCH$_2$ | c-propylmethyl | S-allyl | |
| 5.8 | OCH$_2$ | c-propylmethyl | O—Ph | |
| 5.9 | OCH$_2$ | Ph | O—Ph | R$_f$ (EA): |
| 5.10 | OCH$_2$ | benzyl | S-allyl | |
| 5.11 | OCH$_2$CH$_2$ | Me | S-allyl | |
| 5.12 | OCH$_2$CH$_2$ | Et | O—Ph | |
| 5.13 | OCH$_2$CH$_2$ | 3-allyl | S-allyl | |
| 5.14 | OCH$_2$CH$_2$ | Ph | S-allyl | |
| 5.15 | OCH$_2$CH$_2$ | benzyl | O—Ph | |
| 5.16 | OCH$_2$CH=CH | Me | S-allyl | |
| 5.17 | OCH$_2$CH=CH | Et | O—Ph | |
| 5.18 | OCH$_2$CH=CH | 3-allyl | S-allyl | |
| 5.19 | OCH$_2$CH=CH | Ph | S-allyl | |
| 5.20 | OCH$_2$CH=CH | benzyl | O—Ph | |
| 5.21 | OCH$_2$C≡C | Me | S-allyl | |
| 5.22 | OCH$_2$C≡C | Et | O—Ph | |
| 5.23 | OCH$_2$C≡C | 3-allyl | S-allyl | |
| 5.24 | OCH$_2$C≡C | Ph | S-allyl | |
| 5.25 | OCH$_2$C≡C | benzyl | O—Ph | |

TABLE 6

Compounds according to the invention of the formula (I) in which the substituents and symbols have the following meaning:s
$R^{1c}$ = H   $R^4$ = OH   $R^4$ = OH
$X^3$ = NOR$^3$   Y = CH$_2$   Z = CH$_2$

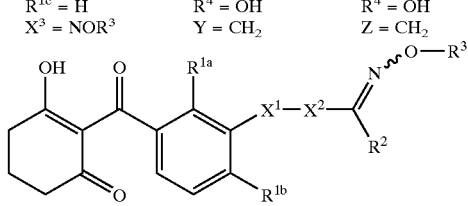

| No. | R$^{1a}$ | R$^{1b}$ | X$^1$–X$^2$ | R$^2$ | R$^3$ | Physical data |
|---|---|---|---|---|---|---|
| 6.1 | Cl | Cl | OCH$_2$ | H | Me | |
| 6.2 | Br | Br | OCH$_2$ | H | Me | |
| 6.3 | Cl | SO$_2$Et | OCH$_2$ | H | Me | R$_f$ (EA): 0.28 |
| 6.4 | Me | SO$_2$Me | OCH$_2$ | H | Me | |
| 6.5 | Cl | Cl | OCH$_2$ | H | Et | |
| 6.6 | Br | Br | OCH$_2$ | H | Et | |
| 6.7 | Cl | SO$_2$Et | OCH$_2$ | H | Et | |
| 6.8 | Br | Br | OCH$_2$ | H | 3-allyl | R$_f$ (EA): 0.31 |
| 6.9 | Cl | SO$_2$Et | OCH$_2$ | H | 3-allyl | |
| 6.10 | Cl | Cl | OCH$_2$ | H | c-propylmethyl | |
| 6.11 | Me | SO$_2$Me | OCH$_2$ | H | c-propylmethyl | |
| 6.12 | Cl | Cl | OCH$_2$ | H | Ph | |
| 6.13 | Br | Br | OCH$_2$ | H | Ph | |
| 6.14 | Cl | SO$_2$Et | OCH$_2$ | H | Ph | |
| 6.15 | Cl | Cl | OCH$_2$ | H | benzyl | |
| 6.16 | Cl | SO$_2$Et | OCH$_2$ | H | benzyl | |
| 6.17 | Cl | Cl | OCH$_2$ | Me | Me | R$_f$ (EA): 0.32 |
| 6.18 | Br | Br | OCH$_2$ | Me | Me | R$_f$ (EA): 0.37 |
| 6.19 | Cl | SO$_2$Et | OCH$_2$ | Me | Me | R$_f$ (EA): 0.16 |
| 6.20 | Me | SO$_2$Me | OCH$_2$ | Me | Me | |
| 6.21 | Cl | Cl | OCH$_2$ | Me | Et | R$_f$ (EA): 0.37 |
| 6.22 | Br | Br | OCH$_2$ | Me | Et | R$_f$ (EA): 0.44 |
| 6.23 | Cl | SO$_2$Et | OCH$_2$ | Me | Et | R$_f$ (EA): 0.12 |

TABLE 6-continued

Compounds according to the invention of the formula (I) in which the substituents and symbols have the following meanings:
$R^{1c} = H$        $R^4 = OH$        $R^4 = OH$
$X^3 = NOR^3$       $Y = CH_2$        $Z = CH_2$

| No. | $R^{1a}$ | $R^{1b}$ | $X^1$–$X^2$ | $R^2$ | $R^3$ | Physical data |
|---|---|---|---|---|---|---|
| 6.24 | Br | Br | OCH$_2$ | Me | 3-allyl | R$_f$ (EA): 0.47 |
| 6.25 | Cl | SO$_2$Et | OCH$_2$ | Me | 3-allyl | R$_f$ (EA): 0.15 |
| 6.26 | Cl | Cl | OCH$_2$ | Me | c-propylmethyl | |
| 6.27 | Me | SO$_2$Me | OCH$_2$ | Me | c-propylmethyl | |
| 6.28 | Cl | Cl | OCH$_2$ | Me | Ph | |
| 6.29 | Br | Br | OCH$_2$ | Me | Ph | |
| 6.30 | Cl | SO$_2$Et | OCH$_2$ | Me | Ph | |
| 6.31 | Br | Br | OCH$_2$ | Me | benzyl | R$_f$ (EA): 0.44 |
| 6.32 | Cl | SO$_2$Et | OCH$_2$ | Me | benzyl | |
| 6.33 | Br | Br | OCH$_2$CH$_2$ | H | Me | |
| 6.34 | Cl | SO$_2$Et | OCH$_2$CH$_2$ | H | Me | |
| 6.35 | Me | SO$_2$Me | OCH$_2$CH$_2$ | H | Me | |
| 6.36 | Cl | Cl | OCH$_2$CH$_2$ | H | Et | |
| 6.37 | Cl | SO$_2$Et | OCH$_2$CH$_2$ | H | Et | |
| 6.38 | Cl | SO$_2$Et | OCH$_2$CH$_2$ | H | 3-allyl | |
| 6.39 | Me | SO$_2$Me | OCH$_2$HC$_2$ | H | c-propylmethyl | |
| 6.40 | Cl | Cl | OCH$_2$CH$_2$ | H | Ph | |
| 6.41 | Br | Br | OCH$_2$CH$_2$ | H | Ph | |
| 6.42 | Br | Br | OCH$_2$CH$_2$ | H | benzyl | |
| 6.43 | Cl | SO$_2$Et | OCH$_2$CH$_2$ | H | benzyl | |
| 6.44 | Br | Br | OCH$_2$CH$_2$ | Me | Me | |
| 6.45 | Cl | SO$_2$Et | OCH$_2$CH$_2$ | Me | Me | |
| 6.46 | Me | SO$_2$Me | OCH$_2$CH$_2$ | Me | Me | |
| 6.47 | Cl | Cl | OCH$_2$CH$_2$ | Me | Et | |
| 6.48 | Cl | SO$_2$Et | OCH$_2$CH$_2$ | Me | Et | |
| 6.49 | Cl | SO$_2$Et | OCH$_2$CH$_2$ | Me | 3-allyl | |
| 6.50 | Me | SO$_2$Me | OCH$_2$CH$_2$ | Me | c-propylmethyl | |
| 6.51 | Cl | Cl | OCH$_2$CH$_2$ | Me | Ph | |
| 6.52 | Br | Br | OCH$_2$CH$_2$ | Me | Ph | |
| 6.53 | Br | Br | OCH$_2$CH$_2$ | Me | benzyl | |
| 6.54 | Cl | SO$_2$Et | OCH$_2$CH$_2$ | Me | benzyl | |
| 6.55 | Br | Br | OCH$_2$CH=CH | H | Me | |
| 6.56 | Cl | SO$_2$Et | OCH$_2$CH=CH | H | Me | |
| 6.57 | Me | SO$_2$Me | OCH$_2$CH=CH | H | Me | |
| 6.58 | Cl | Cl | OCH$_2$CH=CH | H | Et | |
| 6.59 | Cl | SO$_2$Et | OCH$_2$CH=CH | H | Et | |
| 6.60 | Cl | SO$_2$Et | OCH$_2$CH=CH | H | 3-allyl | |
| 6.61 | Me | SO$_2$Me | OCH$_2$CH=CH | H | c-propylmethyl | |
| 6.62 | Cl | Cl | OCH$_2$CH=CH | H | Ph | |
| 6.63 | Br | Br | OCH$_2$CH=CH | H | Ph | |
| 6.64 | Br | Br | OCH$_2$CH=CH | H | benzyl | |
| 6.65 | Cl | SO$_2$Et | OCH$_2$CH=CH | H | benzyl | |
| 6.66 | Br | Br | OCH$_2$CH=CH | Me | Me | |
| 6.67 | Cl | SO$_2$Et | OCH$_2$CH=CH | Me | Me | |
| 6.68 | Me | SO$_2$Me | OCH$_2$CH=CH | Me | Me | |
| 6.69 | Cl | Cl | OCH$_2$CH=CH | Me | Et | |
| 6.70 | Cl | SO$_2$Et | OCH$_2$CH=CH | Me | Et | |
| 6.71 | Cl | SO$_2$Et | OCH$_2$CH=CH | Me | 3-allyl | |
| 6.72 | Me | SO$_2$Me | OCH$_2$CH=CH | Me | c-propylmethyl | |
| 6.73 | Cl | Cl | OCH$_2$CH=CH | Me | Ph | |
| 6.74 | Br | Br | OCH$_2$CH=CH | Me | Ph | |
| 6.75 | Br | Br | OCH$_2$CH=CH | Me | benzyl | |
| 6.76 | Cl | SO$_2$Et | OCH$_2$CH=CH | Me | benzyl | |
| 6.77 | Br | Br | OCH$_2$C≡C | H | Me | |
| 6.78 | Cl | SO$_2$Et | OCH$_2$C≡C | H | Me | |
| 6.79 | Me | SO$_2$Me | OCH$_2$C≡C | H | Me | |
| 6.80 | Cl | Cl | OCH$_2$C≡C | H | Et | |
| 6.81 | Cl | SO$_2$Et | OCH$_2$C≡C | H | Et | |
| 6.82 | Cl | SO$_2$Et | OCH$_2$C≡C | H | 3-allyl | |
| 6.83 | Me | SO$_2$Me | OCH$_2$C≡C | H | c-propylmethyl | |
| 6.84 | Cl | Cl | OCH$_2$C≡C | H | Ph | |
| 6.85 | Br | Br | OCH$_2$C≡C | H | Ph | |
| 6.86 | Br | Br | OCH$_2$ | Et | Me | R$_f$ (EA): 0.29 |
| 6.87 | Cl | Cl | OCH$_2$ | Et | Me | R$_f$ (EA): 0.40 |
| 6.88 | Cl | SO$_2$Et | OCH$_2$ | Et | Me | R$_f$ (EA): 0.17 |
| 6.89 | Cl | Cl | OCH$_2$ | Et | Et | R$_f$ (EA): 0.35 |
| 6.90 | Cl | SO$_2$Et | OCH$_2$ | Et | Et | R$_f$ (EA): 0.14 |
| 6.91 | Br | Br | OCH$_2$ | Et | 3-alkyl | R$_f$ (EA): 0.31 |
| 6.92 | Cl | Cl | OCH$_2$ | Et | 3-alkyl | R$_f$ (EA): 0.45 |
| 6.93 | Cl | Cl | OCH$_2$ | Et | benzyl | R$_f$ (EA): 0.38 |
| 6.94 | Br | Br | OCH$_2$ | Et | benzyl | R$_f$ (EA): 0.12 |
| 6.95 | Cl | SO$_2$Et | OCH$_2$ | Et | benzyl | R$_f$ (EA): 0.15 |

B. Formulation Examples

1. Dust

A dust is obtained by mixing 10 parts by weight of a compound of the formula (I) and 90 parts by weight of talc as inert substance and comminuting the mixture in a hammer mill.

2. Dispersible Powder

A wettable powder which is readily dispersible in water is obtained by mixing 25 parts by weight of a compound of the formula (I), 64 parts by weight of kaolin-containing quartz as inert material, 10 parts by weight of potassium ligninsulfonate and 1 part by weight of sodium oleoylmethyltauride as wetter and dispersant, and grinding the mixture in a pinned-disk mill.

3. Dispersion Concentrate

A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as solvent and 10 parts by weight of oxethylated nonylphenol as emulsifier.

5. Water-dispersible Granules

Water-dispersible granules are obtained by mixing 75 parts by weight of a compound of the formula (I), 10" calcium ligninsulfonate,
  5" sodium lauryl sulfate,
  3" polyvinyl alcohol and
  7" kaolin, grinding the mixture in a pinned-disk mill and granulating the powder in a fluidized bed by spraying on water as granulation liquid.

Water-dispersible granules are also obtained by homogenizing and precomminuting, in a colloid mill, 25 parts by weight of a compound of the formula (I),
  5" sodium 2,2'-dinaphthylmethane-6,6'-disulfonate,
  2" sodium oleoylmethyltauride, 1" polyvinyl alcohol,
17" calcium carbonate and
50" water,
subsequently grinding the mixture in a bead mill, and atomizing and drying the resulting suspension in a spray tower by means of a single-substance nozzle.

C. Biological Examples

1. Post-emergence Herbicidal Action Against Harmful Plants

Seeds of mono- and dicotyledonous harmful plants are placed in sandy loam in cardboard pots, covered with soil and grown in the greenhouse under good growth conditions. 2 to 3 weeks after sowing, the test plants are treated in the three-leaf stage. The compounds according to the invention, which are formulated as wettable powders or as emulsion concentrates, are sprayed at various dosages onto the surface of the green plant parts at an application rate of 600 to 800 l of water per ha (converted). After the test plants have been left to stand in the greenhouse for 3 to 4 weeks under optimal growth conditions, the effect of the compounds is scored visually. The chosen compounds according to the invention have an outstanding activity against a broad spectrum of economically important monocotyledonous and dicotyledonous harmful plants. Thus, for example, the compounds of examples Nos. 3.3 and 1.8 exhibit, at a dosage of 320 g/ha, 90–100% activity against Chenopodium album, Echinocloa crus galli and Veronica persica. The compounds of examples Nos. 4.19 and 4.98 exhibit, at 80 g/ha, 90–100% activity against Stellaria media, Chenopodium album and Matricaria inodora.

2. Plant Tolerance

In further greenhouse experiments, seeds of crop plants and of monocotyledonous and dicotyledonous harmful plants are placed in sandy loam, covered with soil and placed in the greenhouse until the plants have developed two to three true leaves. Then, they are treated with the compounds of the formula (I) according to the invention as described above under item 1. Four to five weeks after the application and after having been left to stand in the greenhouse, visual scoring reveals that the compounds according to the invention are outstandingly well tolerated by important crop plants, in particular wheat, maize and rice. Thus, for example, the compounds of examples Nos. 4.16 and 4.98 cause, at a dosage of 320 g/ha, no damage in wheat, rice and maize. The compounds of examples Nos. 1.4, 1.8, 4.16, 4.19 and 4.98 caused, at 80 g/ha, no damage in wheat, rice and maize.

What is claimed is:

1. A compound of the formula (I) or a salt thereof

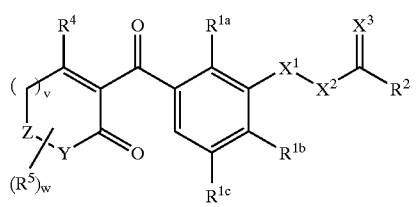

where the radicals and indices are as defined below:

$X^1$ is a divalent unit selected from the group consisting of O, $S(O)_n$, N—H, and N—$R^2$;

$X^2$ is a straight-chain or branched $(C_1-C_6)$-alkylene, $(C_2-C_6)$-alkenylene or $(C_2-C_6)$-alkynylene chain which is substituted by w radicals selected from the group consisting of halogen, cyano and $NO_2$ and by v radicals $R^2$;

$X^3$ is oxygen, sulfur or $NOR^3$;

$R^{1a}$, $R^{1b}$ and $R^{1c}$ independently of one another are H, mercapto, $NO_2$, halogen, cyano, thiocyanato, $(C_1-C_6)$-alkyl-CO—O, $(C_1-C_6)$-alkyl-$S(O)_n$—O, $(C_1-C_6)$-alkyl-$S(O)_n$, $(C_1-C_6)$-haloalkyl-$S(O)_n$, $(C_3-C_7)$-cycloalkyl-$S(O)_n$, di-$(C_1-C_6)$-alkyl-N—$SO_2$, $(C_1-C_6)$-alkyl-$SO_2$—NH, $(C_1-C_6)$-alkyl-NH—CO, di-$(C_1-C_6)$-alkyl-N—CO, $(C_1-C_6)$-alkyl-$SO_2$-$(C_1-C_6)$-alkyl-NH, $(C_1-C_6)$-alkyl-CO—$(C_1-C_6)$-alkyl-NH, $(C_1-C_6)$-alkyl-O—$CH_2$, $(C_1-C_6)$-alkyl-$S(O)_n$—$CH_2$, $(C_1-C_6)$-alkyl-NH—$CH_2$, 1,2,4-triazol-1-yl, 1,2,4-triazol-1-yl-$CH_2$, $(C_1-C_6)$-alkyl-$(D)_p$, $(C_2-C_6)$-alkenyl-$(D)_p$, $(C_2-C_6)$-alkynyl-$(D)_p$, $(C_3-C_9)$-cycloalkyl-$(D)_p$, $(C_3-C_9)$-cycloalkenyl-$(D)_p$, $(C_1-C_6)$-alkyl-cycloalkyl-$(D)_p$, or $(C_1-C_6)$-alkyl-cycloalkenyl-$(D)_p$, each of which is substituted by v radicals selected from the group consisting of CN, $NO_2$ and halogen;

D is oxygen or sulfur;

$R^2$, $R^3$ independently of one another are hydrogen, $(C_1-C_6)$-alkyl, $(C_2-C_6)$-alkenyl, $(C_2-C_6)$-alkynyl, $(C_3-C_9)$-cycloalkyl, $(C_3-C_9)$-cycloalkenyl, $(C_1-C_6)$-alkyl-$(C_3-C_9)$-cycloalkyl, $(C_1-C_6)$-alkyl-$(C_3-C_9)$-cycloalkenyl, $(C_2-C_6)$-alkenyl-$(C_3-C_9)$-cycloalkyl, $(C_2-C_6)$-alkenyl-$(C_3-C_9)$-cycloalkenyl, $(C_2-C_6)$-alkynyl-$(C_3-C_9)$-cycloalkyl, $(C_2-C_6)$-alkynyl-$(C_3-C_9)$-cycloalkenyl or straight-chain or branched $[C(R^6)_2]_z$—$[OC(R^6)_2]_w$-$[O-C(R^6)_2]_x$-$R^6$, each of which is substituted by v radicals selected from the group consisting of CN, $NO_2$ and halogen, aryl, $(C_1-C_6)$-alkyl-aryl, $(C_2-C_6)$-alkenyl-aryl, $(C_2-C_6)$-alkynyl-aryl, heterocyclyl or heteroaryl, each of which is substituted by v radicals selected from the group consisting of CN, $NO_2$, halogen, $(C_1-C_6)$-alkyl-$(D)_p$ and halo-$(C_1-C_6)$-alkyl-$(D)_p$;

$R^4$ is $OR^7$, $(C_1-C_4)$-alkylthio, halo-$(C_1-C_4)$-alkylthio, $(C_2-C_4)$-alkenylthio, halo-$(C_2-C_4)$-alkenylthio, $(C_2-C_4)$-alkynylthio, halo-$(C_2-C_4)$-alkynylthio, $(C_1-C_4)$-alkyl-SO, halo-$(C_1-C_4)$-alkyl-SO, $(C_2-C_4)$-alkenyl-SO, halo-$(C_2-C_4)$-alkenyl-SO, $(C_2-C_4)$-alkynyl-SO, halo-$(C_2-C_4)$-alkynyl-SO, $(C_1-C_4)$-alkyl-$SO_2$, halo-$(C_1-C_4)$-alkyl-$SO_2$, $(C_2-C_4)$-alkenyl-$SO_2$, halo-$(C_2-C_4)$-alkenyl-$SO_2$, $(C_2-C_4)$-alkynyl-$SO_2$, halo-$(C_2-C_4)$-alkynyl-$SO_2$, halogen, CN, cyanato, thiocyanato or phenylthio;

$R^5$ is hydrogen, tetrahydropyran-3-yl, tetrahydropyran-4-yl, tetrahydrothiopyran-3-yl, $(C_1-C_4)$-alkyl, $(C_1-C_8)$-cycloalkyl, $(C_1-C_4)$-alkoxy, $(C_1-C_4)$-alkoxy-$(C_1-C_4)$-alkyl, $(C_1-C_4)$-alkoxy-CO, $(C_1-C_4)$-alkylthio or phenyl, each of which is substituted by v radicals selected from the group consisting of halogen, $(C_1-C_4)$-alkylthio and $(C_1-C_4)$-alkoxy, or two radicals $R^5$ attached to a common carbon atom form a chain selected from the group consisting of $OCH_2CH_2O$, $OCH_2CH_2CH_2O$, $SCH_2CH_2S$ and $SCH_2CH_2CH_2S$, which is substituted by w methylene groups, or two radicals $R^5$ attached to directly adjacent carbon atoms form, together with the carbon atoms carrying them, a 3- to 6-membered ring substituted by w radicals selected from the group consisting of halogen, $(C_1-C_4)$-alkyl, $(C_1-C_4)$-alkylthio and $(C_1-C_4)$-alkoxy;

$R^6$ is H, halogen, CN, $NO_2$, $(C_1-C_4)$-alkyl or halo-$(C_1-C_4)$-alkyl;

$R^7$ is H, $(C_1-C_4)$-alkyl, halo-$(C_1-C_4)$-alkyl, $(C_1-C_4)$-alkoxy-$(C_1-C_4)$-alkyl, CHO, $(C_1-C_4)$-alkyl-CO, ($C_1$–$C_4$)-alkoxy-CO, ($C_1$–$C_4$)-alkyl-NH—CO, di-($C_1$–$C_4$)-alkyl-N—CO, ($C_1$–$C_4$)-alkyl-SO$_2$, halo-($C_1$–$C_4$)-alkyl-SO$_2$, is benzoyl or phenyl-SO$_2$, each of which is substituted by v radicals selected from the group consisting of ($C_1$–$C_4$-alkyl, halo-($C_1$–$C_4$)-alkyl, ($C_1$–$C_4$)-alkoxy, halo-($C_1$–$C_4$)-alkoxy, halogen, CN and NO$_2$;

Y is a divalent unit selected from the group consisting of O, S, N—H, ($C_1$–$C_6$)-alkyl-N, CHR$^5$ and C(R$^5$)$_2$;

Z is a direct bond or a divalent unit selected from the group consisting of O, S, SO, SO$_2$, N—H, ($C_1$–$C_6$)-alkyl-N, CHR$^6$ and C(R$^6$)$_2$;

m and n are each independently of one another 0, 1 or 2;

p is independently of the other p 0 or 1;

v is 0, 1, 2 or 3;

w and x are each independently of one another 0, 1, 2, 3 or 4;

z is 1, 2, 3 or 4, where w and x are not simultaneously zero.

2. A compound as claimed in claim 1, in which R$^2$, R$^3$ are independently of one another hydrogen, ($C_1$–$C_6$)-alkyl, ($C_2$–$C_6$)-alkenyl, ($C_2$–$C_6$)-alkynyl, ($C_3$–$C_9$)-cycloalkyl, ($C_3$–$C_9$)-cycloalkenyl, ($C_1$–$C_6$)-alkyl-($C_3$–$C_9$)-cycloalkyl, ($C_1$–$C_6$)-alkyl-($C_3$–$C_9$)-cycloalkenyl, ($C_2$–$C_6$)-alkenyl-($C_3$–$C_9$)-cycloalkyl, ($C_2$–$C_6$)-alkenyl-($C_3$–$C_9$)-cycloalkenyl, ($C_2$–$C_6$)-alkynyl-($C_3$–$C_9$)-cycloalkyl, ($C_2$–$C_6$)-alkynyl-($C_3$–$C_9$)-cycloalkenyl or straight-chain or branched [C(R$^6$)$_2$]$_z$—[OC(R$^6$)$_2$]$_w$—[O—C(R$^6$)$_2$]$_x$—R$^6$, each of which is substituted by v radicals selected from the group consisting of CN, NO$_2$ and halogen, aryl, ($C_1$–$C_6$)-alkyl-aryl, ($C_2$–$C_6$)-alkenyl-aryl or ($C_2$–$C_6$)-alkynyl-aryl, each of which is substituted by v radicals selected from the group consisting of CN, NO$_2$, halogen, ($C_1$–$C_6$)-alkyl-(D)$_p$ and halo-($C_1$–$C_6$)-alkyl-(D)$_p$;

X$^3$ is oxygen or NOR$^3$, and

R$^{1c}$ is hydrogen.

3. The compound as claimed in claim 1, in which

X$^1$ is oxygen or S(O)$_n$;

R$_{1a}$, R$_{1b}$ are independently of one another F, Cl, Br, NO$_2$, CF$_3$, CH$_3$, CH$_3$S, CH$_3$O, CH$_3$SO$_2$, EtSO$_2$, CF$_3$CH$_2$SO$_2$ or cyclopropyl-SO$_2$, and R$^2$, R$^3$ are independently of one another hydrogen, ($C_1$–$C_6$)-alkyl, ($C_2$–$C_6$)-alkenyl, ($C_2$–$C_6$)-alkynyl, ($C_3$–$C_9$)-cycloalkyl, ($C_1$–$C_6$)-alkyl-($C_3$–$C_9$)-cycloalkyl, straight-chain or branched [C(R$^6$)$_2$]$_z$—[OC(R$^6$)$_2$]$_w$—[O—C(R$^6$)$_2$]$_x$—R$^6$, each of which is substituted by v radicals selected from the group consisting of CN, NO$_2$ and halogen, aryl or ($C_1$–$C_6$)-alkyl-aryl, each of which is substituted by v radicals selected from the group consisting of CN, NO$_2$, halogen, ($C_1$–$C_6$)-alkyl-(D)$_p$ and halo-($C_1$–$C_6$)-alkyl-(D)$_p$.

4. The compound as claimed in claim 1, in which

X$^1$ is oxygen and

R$^4$ is OR$^7$, ($C_1$–$C_4$)-alkylthio, ($C_2$–$C_4$)-alkenylthio, ($C_1$–$C_4$)-alkyl-SO$_2$, halogen, CN, cyanato, thiocyanato or phenylthio.

5. The compound as claimed in claim 1, in which R$^5$ is hydrogen or ($C_1$–$C_4$)-alkylthio.

6. The compound as claimed in claim 1, in which

R$^4$ is OR$^7$;

D is oxygen;

Y, Z are each CH$_2$;

v, w and x are each independently of one another 0, 1 or 2;

z is 1 or 2.

7. The compound as claimed in claim 1 which is not present as a salt.

8. A herbicidal composition which comprises a herbicidally effective amount of at least one compound of the formula (I) as claimed in claim 1.

9. The herbicidal composition as claimed in claim 8 in a mixture with formulation auxiliaries.

10. A method for controlling unwanted plants which comprises applying an effective amount of at least one compound of the formula (I) as claimed in claim 1 to the plants or to the location of the unwanted plants.

11. The method as claimed in claim 10, wherein the unwanted plants are located in crops of useful plants and the at least one compound of the formula (I) is applied to both the unwanted plants are transgenic useful plants.

12. The method as claimed in claim 11, wherein the useful plants are transgenic useful plants.

13. A method for controlling unwanted plants which comprises applying an effective amount of a herbicidal composition as claimed in claim 8 to the plants or to the location of the unwanted plants.

14. A method for controlling unwanted plants which comprises applying an effective amount of a herbicidal composition as claimed in claim 9 to the plants or to the location of the unwanted plants.

15. The method as claimed in claim 13, wherein the unwanted plants are located in crops of useful plants and the herbicidal composition is applied to both the unwanted plants and the useful plants.

16. A method as claimed in claim 15, wherein the useful plants are transgenic useful plants.

* * * * *

UNITED STATES PATENT AND TRADEMARK OFFICE
CERTIFICATE OF CORRECTION

PATENT NO.     : 6,930,208 B2
DATED          : August 16, 2005
INVENTOR(S)    : Seitz et al.

Page 1 of 1

It is certified that error appears in the above-identified patent and that said Letters Patent is hereby corrected as shown below:

<u>Column 34,</u>
Line 34, "the unwanted plants are transgenic useful plants" should read -- the unwanted plants and the useful plants. --.

Signed and Sealed this

Twenty-second Day of November, 2005

JON W. DUDAS
*Director of the United States Patent and Trademark Office*